United States Patent [19]

Martino

[11] Patent Number: 5,805,676
[45] Date of Patent: Sep. 8, 1998

[54] TELEPHONE/TRANSACTION ENTRY DEVICE AND SYSTEM FOR ENTERING TRANSACTION DATA INTO DATABASES

[75] Inventor: Rocco L. Martino, Villanova, Pa.

[73] Assignee: PCPI Phone, Inc., Villanova, Pa.

[21] Appl. No.: 446,546

[22] Filed: May 19, 1995

[51] Int. Cl.[6] .............................................. H04M 11/00
[52] U.S. Cl. .................................. 379/93.17; 379/93.25; 379/93.01; 395/203
[58] Field of Search .................................. 379/89, 90, 94, 379/96, 98, 202, 88, 110, 93, 87; 364/400, 401 M; 381/110; 348/13, 14; 395/201–204

[56] References Cited

U.S. PATENT DOCUMENTS

| | | | |
|---|---|---|---|
| 4,591,662 | 5/1986 | Legros et al. | 179/2 DP |
| 4,598,171 | 7/1986 | Hanscom et al. | 381/110 |
| 4,689,478 | 8/1987 | Hale et al. | 379/96 |
| 4,776,016 | 10/1988 | Hansen | 381/110 |
| 4,835,372 | 5/1989 | Gombrich et al. | 379/93 |
| 4,851,999 | 7/1989 | Moriyama | 364/400 |
| 4,858,121 | 8/1989 | Barber et al. | 395/202 |
| 4,860,342 | 8/1989 | Danner | 379/96 |
| 4,972,462 | 11/1990 | Shibata | 379/89 |
| 4,984,155 | 1/1991 | Geier et al. | 364/401 |
| 4,991,199 | 2/1991 | Parekh et al. | 379/97 |
| 5,008,927 | 4/1991 | Weiss et al. | 379/98 |
| 5,189,632 | 2/1993 | Paajanen et al. | 364/705.05 |
| 5,195,086 | 3/1993 | Baumgartner et al. | 379/202 |
| 5,195,130 | 3/1993 | Weiss et al. | 379/98 |
| 5,301,105 | 4/1994 | Cummings, Jr. | 364/401 M |
| 5,333,266 | 7/1994 | Boaz et al. | 379/89 |
| 5,351,076 | 9/1994 | Hata et al. | 348/14 |
| 5,365,577 | 11/1994 | Davis et al. | 379/96 |
| 5,416,831 | 5/1995 | Chewning, III et al. | 379/96 |
| 5,572,421 | 11/1996 | Altman et al. | 395/203 |

OTHER PUBLICATIONS

"a New Generation Of Information Terminals" Ceremtek Electronics Brochure, Apr. 1987.

Primary Examiner—Curtis Kuntz
Assistant Examiner—Stephen W. Palan
Attorney, Agent, or Firm—Woodcock Washburn Kurtz Mackiewicz & Norris LLP

[57] ABSTRACT

A data transaction processing system in which transaction data is entered by the user in response to prompts in a template which is tailored to each user application. The template and entered data are accumulated into data transactions which are immediately transmitted upon completion to an external database server for processing and storage. The data transactions are not locally stored for processing, and no conventional operating system is necessary. No local processing needs to be provided, and the only local storage is a flash PROM which stored the control firmware, a flash memory which stores the data streams making up the forms and menus, and a small RAM which operates as an input/output transaction buffer for storing the data streams of the template and the user replies to the prompts during assembly of a data transaction. The data transaction is received via standard protocols at a database server which, depending upon the application, stores the entire data transaction, explodes the data transaction to produce ancillary records which are then stored, and/or forwards the data transaction or some or all of the ancillary records to other database servers for updating other databases associated with those database servers. Also, in response to requests from the transaction entry device, the database server may return data streams for use in completing the fields in the data transaction or in presenting a menu on the display which was read in from the database server or a remote phone mail system. The transaction entry device is integrated with a telephone and is accessed via a touch screen, an optional keyboard, a magnetic card reader, voice entry, a modem, and the like.

44 Claims, 12 Drawing Sheets

TELEPHONE/TRANSACTION ENTRY DEVICE AND SYSTEM FOR ENTERING TRANSACTION DATA INTO DATABASES

BACKGROUND OF THE INVENTION

1. Field of the Invention

The present invention relates to a system for automatically capturing data at the point of transaction and storing that data in the appropriate database(s), and more particularly, to a data transaction processing system including a transaction entry device which can selectively operate in a telephone mode and a transaction entry mode. In the telephone mode, the transaction entry device operates as a conventional telephone. However, in the transaction entry mode, menus are used to navigate the user to forms which facilitate the entry of data. The entered data and forms together form data transactions which are transmitted to one or more databases for processing and storage. The database(s) also "explodes" the data transactions into their component parts and transmits those component parts to still other databases for processing and storage so that the data in the data transactions automatically updates all current database items affected by such data.

2. Description of the Prior Art

The telephone has become an increasingly versatile instrument. The functionality of telephones has been expanded by incorporating the functions of answering machines, facsimile machines, and the like. Point-of-entry systems have also been developed which incorporate computer processing capabilities into conventional telephones. For example, a computer/telephone apparatus is described in U.S. Pat. Nos. 5,195,130, 5,008,927, and 4,991,199 which configures a telephone as a programmable microcomputer which is operated through the standard telephone 12-key keypad. A programmable gate array is reconfigured to accommodate various types of software which require different hardware configurations but without actually reconfiguring the hardware. The reconfiguration data is received from a network host computer and is used by the programmable microcomputer to emulate the hardware of any of a plurality of service bureaus which communicate with the network host computer. In this manner, the telephone/computer is configured to communicate data to/from any of a number of different service bureaus via conventional telephone lines.

However, telephone/computer systems of the type described in the afore-mentioned patents are typically quite complicated and expensive and are limited by the types of operating software which can be downloaded from the network host computer. Also, such telephone/computer systems are relatively slow since the microcomputer must be reconfigured before it will permit communication with the requested service bureau. Because of these characteristic features, such telephone/computer systems are typically used in public locations and are not efficient for creating point-of-entry transactions in typical commercial or private settings. A point-of-entry transaction system is desired which does not have such limitations and which is operating system independent.

Elimination of the requirement of a conventional operating system and the associated application programs for the microcomputer of a data entry device would greatly decrease the cost of such a device. However, to date, this has not been possible because the operating system is needed to run the application programs which control the data communications and together handle discrete parts of the system. Unfortunately, such application programs require substantial amounts of local memory and substantial processing power for performing the desired functions. Also, the operating systems themselves tend to be quite costly to purchase and maintain.

Accordingly, a data entry system is desired which does not have the inherent limitations of conventional point-of-entry systems such as the requirement of a standard operating system for communication with a remote service bureau or file server. A data entry device and associated system is desired which performs a minimal amount of processing at the data entry device so that the data entry device may be as simple and inexpensive as possible, thereby bringing the cost of such a device into a range suitable for most commercial and private uses. It is also preferable that such a data entry device provide a wide range of functionality without requiring a local operating system program and a plurality of applications programs for implementing each function. The present invention has been designed to meet these needs.

SUMMARY OF THE INVENTION

The system which meets the above-mentioned needs in the art includes a transaction entry device that permits the user to organize and control all aspects of his or her personal transactions as well as any transactions that may occur in an office setting. In its simplest terms, the transaction entry device formats input data into a data transaction having content which is dependent upon the type of application to which the associated data pertains. These data transactions are then transferred to a local or remote database server which "explodes" each data transaction into its component parts for updating all databases containing data to which the data in the component parts pertain. In this "transaction entry mode" the transaction entry device of the invention functions as a multi-purpose workstation. However, since the data transactions are created without the use of an operating system or application programs, the transaction entry device is quite simple and inexpensive and may be readily integrated with the customer's desktop telephone or portable telephone.

The present invention combines computer technology and telephone technology to allow transaction data to be captured at the point of initiation of the transaction. The transaction entry device is integrated into a conventional telephone which acts as either a normal telephone in a telephone mode or as a transaction entry device in a transaction entry mode. When in telephone mode, the telephone operates in a conventional manner. However, when in transaction entry mode, the transaction entry device is driven by a microprocessor which is, in turn, driven by an operating system independent transaction assembly (or application) server (TAS) comprised of data streams stored in a flash PROM. The TAS is absolutely self-contained in its relationship to the hardware of the transaction entry device and in general performs the two basic functions of (1) generating a template or form from a data stream and (2) developing a data transaction as the user inputs data in response to prompts in the template or form. The template is a series of data streams read from a local flash memory or transmitted directly from an external source such as a database file server.

During operation, the data entered by the user in response to prompts in the template are accumulated into data transactions which are immediately transmitted to an external database server. Unlike typical prior art systems, the data transactions are not locally stored for processing by the local microprocessor once the data transaction has been completed. On the contrary, the only required storage in the transaction entry device is a flash PROM for storing the TAS firmware, a flash memory for storing the data streams used by the TAS firmware to complete a form and the modem numbers for the remote database servers, and a small RAM which operates as an input/output transaction buffer for storing the data streams of the template and the user replies to the prompts in the template during assembly of a data transaction. The transaction buffer(s) only needs to be as large as the largest data transaction since it only stores the form until the entire data transaction is completed. In this sense, the transaction entry device serves as an assembly point for specific transactions until they are ready for transmission to an external database server for processing and storage.

The data transaction formed by the transaction entry device is transmitted via modem to a local or remote database server for processing and storage. The data transaction is received via standard protocols at the database server which, depending upon the application, stores the entire data transaction, explodes the data transaction to produce ancillary records which are then stored, and/or forwards the data transaction or some or all of the ancillary records to other database servers for updating other databases associated with those database servers. Also, in response to requests from the transaction entry device, any of the database servers may send data streams back to the transaction entry device for use in completing the fields in the data transaction or in displaying new forms or menus for selection.

Thus, the data transaction system of the invention comprises at least three tiers: a first tier for capturing the data transaction from the user, where the data transaction has a one-to-many relationship to file structures; a second tier for exploding the data transaction into its component parts on a system-specific basis so that each component part has a one-to-one correspondence with a file; and a third tier for providing additional explosions of the data transactions on an application-specific basis so that each application has its own set of data transactions.

A preferred embodiment of the transaction entry device of the invention resembles a conventional telephone except that it includes a touch screen and an optional keyboard for data entry in addition to the conventional numeric and function keypad inputs. A telephone handset or headset is optional and may be replaced by a microphone and speaker. The transaction entry device of the invention also includes RS-232 and other input/output ports for accommodating other options such as a wireless (RF) receiver, a magnetic card and/or smart card reader, a video camera and video display, infrared controllers, and the like. The telephone preferably has normal touch-tone functions as well as mobile and cellular options.

Preferably, the transaction entry device contains a microprocessor such as an Intel 80386SX or higher, one megabyte of flash memory for dynamically storing the data streams for the templates, one megabyte of flash PROM for storing the TAS firmware, and a 128 kB RAM which functions as a transaction buffer for storing the data streams of the templates and the user responses until completion of the data transaction. A graphics display screen is also provided for displaying the templates to the user for the entry of the data which will form the data transactions. Preferably, the graphics display screen is on the order of 24 lines by 40 characters for a desktop unit and 12 lines by 40 characters for a cellular unit.

The transaction assembly (application) server (TAS) guides the user to the desired template via menu selections, where the menus and templates are stored in flash memory as data streams and are called up by the TAS firmware when selected by the user. Generally, the menus are treated as a special type of template or form. The templates stored in the flash memory may be updated at any time to handle particular applications by reading in a new data set which has been created off-line and downloaded via modem or direct connection to the flash memory of the transaction entry device. Alternatively, the data may be downloaded to an RS-232 input. The same connections may be used to provide an automatic read from a remote database or an automatic write to a remote database. New applications may be added simply by adding additional flash memory elements containing the necessary templates for the new application.

The telephone/transaction entry device and the associated system for storing transaction data in accordance with the invention is unique in that it separates the user from the database and provides a simple, user friendly way to enter transaction data without requiring a local operating system to run various application programs. Since all data is entered as data transactions determined by templates tailored to particular applications, the user applications may be generalized so that no unique user application programs need to be written when a new application is added. However, if code is needed, or if a multimedia element is to be included in a data transaction, it can be appended to a data transaction as an additional parameter stream in the stream of data forming the data transaction. Also, since the nature of the data in the respective fields of the templates for particular applications is known in advance, the interface to a database server to permit storage of the data transactions and their component parts in the appropriate databases in the appropriate formats for each database becomes trivial.

In an alternative implementation of the invention, a process may be selected from the menu of the transaction entry device which creates a "visible" menu corresponding to a voice mail menu of a remote phone mail system. When such a process is selected, the telephone or modem interface makes a telephone connection to the remote phone mail system, and, once the connection is made, the data transaction assembler sends a data request for a visual representation of the phone mail menu of the remote phone mail system via the telephone connection to the remote phone mail system. A data stream containing the visual representation of the phone mail menu from the remote phone mail system is then returned via the telephone connection and stored in a memory of the transaction entry device for presentation to the display screen of the transaction entry device 12. When the desired phone mail menu option is selected from the "visible" voice mail menu, the data transaction assembler creates a data transaction indicating which menu item was selected and sends the data transaction to the remote phone mail system via the telephone connection. Based on the menu selection, the remote phone mail system then returns a data stream containing a visual representation of the next phone mail menu via the telephone connection for storage and display. This process is repeated until the calling party is required to leave a message or the called party is reached.

BRIEF DESCRIPTION OF THE DRAWINGS

The above-mentioned characteristic features of the invention will become more apparent to those skilled in the art in view of the following detailed description of the invention, of which.

DETAILED DESCRIPTION OF THE PRESENTLY PREFERRED EMBODIMENT

Figure 1:
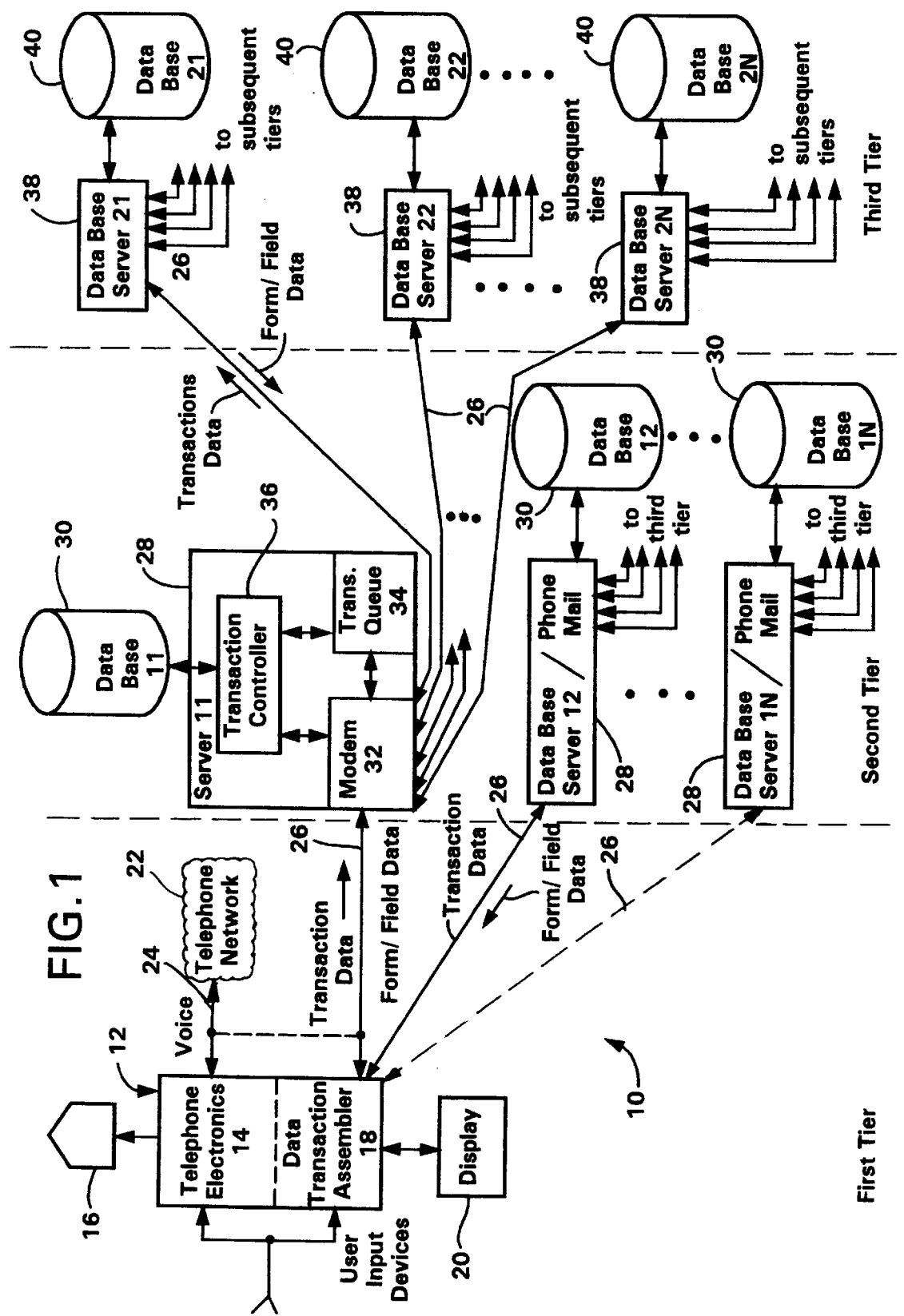
FIG. 1 is a schematic diagram of a system for entering data transactions into databases in accordance with the invention.

A system and method which meets the above-mentioned objects and provides other beneficial features in accordance with the presently preferred exemplary embodiment of the invention will be described below with reference to FIGS. 1–10. Those skilled in the art will readily appreciate that the description given herein with respect to those figures is for explanatory purposes only and is not intended in any way to limit the scope of the invention. For example, those skilled in the art will appreciate that the telephone/transaction entry device and system for entering data transactions into remote databases in accordance with the invention may be used in numerous settings in numerous applications. Accordingly, all questions regarding the scope of the invention should be resolved by referring to the claims.

A. SYSTEM DESCRIPTION

1. Overview

The system of the invention provides for the automatic capture and computerization of data associated with data transactions as they occur. As used herein, a data transaction is the combination of a form or template or a series of forms or templates containing data entry prompts and the data entered in response to those prompts. Throughout the remainder of this specification, the words "form" and "template" will be used interchangeably.

The data transactions are generated by a transaction entry device through an interactive process between the user and the form. The data transaction is assembled in a transaction buffer in the data transaction entry device and then transmitted to an external database for storage. No local storage for data transactions is available. The data transaction is defined externally by the database in that all applications consist of a series of customized forms and prompts for soliciting entry of the data needed to update the databases containing data related to the particular application. Generally, the data transaction will have a one-to-many relationship to the file structures of the database containing data for that application.

The data transactions are entered using the transaction entry device. Preferably, the transaction entry device is integrated with telephone electronics so that the resulting device may selectively operate as a conventional telephone or as a data transaction entry device. The resulting transaction entry device preferably includes a touch screen and/or keyboard which provides input to a transaction assembly (application) server (TAS) which, in turn, presents selection options via menus and forms for completion by the user. Menu and form selection and form completion is made by touch, by key selection from the keyboard, by moving a cursor to the appropriate selection point and depressing a key, or even by voice command. Whenever data entry (other than mere selection) is desired, it is accomplished via a menu-driven selection process and/or by direct entry of data using a keyboard, a keypad, a touch screen, and the like. In the menu-driven case, a set of options is presented to the display screen by the TAS firmware. If this set of options exceeds the capacity of the display screen, then the list is scrolled up or down through the use of scroll keys on the device, by voice command, or by touch at scroll command points. Once the selection is made, the data associated with that selection is automatically entered into the form from a local or remote database, or the data is input by the user. In the event of keyboard entry, the TAS firmware may present a keyboard at the bottom of the display screen for touch entry; alternately, an optional keyboard located at the base of the transaction entry device may be used.

When the data is entered independently of a selection process, such data also may be entered using a swipe card if the data resides on the swipe card or the data may be transferred into the data transaction via modem from an external source. The data read from the swipe card can be used to fill out a form or may be transmitted to an external database or computer. Data returned from the external database or computer via modem may also be used to fill out the fields in the form. As desired, the data in a data transaction may also be written to a swipe card or memory card and the like.

The TAS firmware of the invention stores the options as well as control programs (microcode) for the processor for use with the templates in creating the data transactions. The TAS firmware also includes a program allowing connection via modem to one or more external computers and databases. Preferably, two modes of operation are available: transaction entry mode (with or without modem connection) and telephone mode. A selection of either the transaction entry mode or the telephone mode is made through a switch selection on the transaction entry device.

When the transaction entry device is placed in the transaction entry mode, the TAS firmware immediately presents a selection menu for all of the options the system is programmed to handle. In the telephone mode, on the other hand, a dial tone is provided and the telephone keypad is enabled. In telephone mode, one or more lines may be connected so as to allow simultaneous use of the transaction entry device without interfering with the modem connection. However, if a single telephone line is used, the telephone capability is available at all times or intermittently via modem as specified by the particular application. In the intermittent mode, upon a "save" the transaction entry device will control a dial up and transfer of data to a remote database server. On the other hand, if the telephone is used with an automatic dialer mechanism utilizing a phone list, the transaction entry device may automatically change from the telephone mode to the transaction entry mode. In this case, a display on the telephone may be used to present a name and telephone list from which a selection can be made in accordance with the menu selection techniques described below.

2. Data Transaction System (FIGS. 1–4)

FIG. 1 is a schematic diagram of a system 10 for entering data transactions into databases in accordance with the invention. As illustrated, system 10 comprises a first tier for capturing a data transaction having a one-to-many relationship to file structures, a second tier for exploding the data transaction into component parts having a one-to-one relationship to file structures, and a third tier for providing additional explosion of the data transactions for specific applications.

The first tier comprises a transaction entry device 12 which captures the data transaction from the user in response to any of a plurality of inputs from the user. Transaction entry device 12 includes conventional telephone electronics 14 and speaker 16 and a data transaction assembler 18 for creating a data transaction in accordance with the invention. A display screen 20 is preferably associated with data transaction assembler 18 so that the user may monitor creation of each data transaction. Telephone electronics 14 are connected to a telephone switching network 22 via a conventional voice connection 24 over the telephone lines, while data transaction assembler 18 is connected via telephone lines 26 to one or more database servers 28. As illustrated in FIG. 1, telephone lines 24 and 26 may be separate lines, thereby permitting simultaneous use of the telephone and data entry functions, or the telephone electronics 14 and data transaction assembler 18 may be connected to a single line as illustrated in phantom in FIG. 1. Of course, when the telephone electronics 14 and data transaction assembler 18 are connected to a single line, a mode switch will enable their mutually exclusive operation, or alternatively, any of a number of conventional transmission schemes may be used to permit simultaneous transmission of the voice from the telephone electronics 14 and the data from the data transaction assembler 18 over the same line.

During operation in the transaction entry mode, transaction entry device 12 is responsive to user input devices such as a touch screen, a telephone keypad, a keyboard, a microphone, a swipe card, a memory card, video input, and the like, to form data transactions using data transaction assembler 18. Alternatively, the transaction entry device 12 operates in a telephone mode as a conventional telephone and receives inputs from a microphone and/or a handset, a touch tone keypad, and the like. More details of the transaction entry device 12 and data transaction assembler 18 will be provided in the next section with respect to FIGS. 5–10.

The second tier comprises one or more database servers 28 and their associated databases 30. In general, each database server 28 receives data transactions from one or more transaction entry devices 12 and "explodes" the received data transactions into their component parts for storage in the appropriate files of the associated database 30. In other words, the one-to-many file structure of the data transactions from one or more transaction entry devices 12 is converted into many one-to-one data transactions for storage in individual files of database 30.

Each database server 28 includes a modem 32 for transmitting/receiving data from the telephone lines 26, particularly the data transactions from one or more transaction entry devices 12. Preferably, the data transactions are transmitted over the telephone lines 26 as data packets having, for example, 128 bytes, where 120 bytes contain information and 8 bytes contain control data. A transaction queue 34 acts as an input buffer for the received data transactions and controls the rate of presentation of the data transactions to transaction controller 36. Transaction controller 36 processes the received data transactions to extract the physical file relationships of the component parts of the data transactions and stores the components parts and different combinations thereof in the appropriate files of associated database 30. Alternatively, transaction controller 36 may process a data request from data transaction assembler 18 requesting information from database 30 for completing certain fields of a data transaction being processed by the transaction entry device 12. Database 30 then provides the requested information to database server 28 which, via modem 32, provides a data stream back to data transaction assembler 18 for use in completing the data transactions or presenting additional menus and forms in accordance with the invention. Typically, a user ID and password are transmitted to the transaction controller 36 to permit a connection to be made by data transaction assembler 18. Thus, transaction controller 36 also checks and stores startup and logoff information in addition to storing data transactions and directing reconstituted data transactions to other database servers as described herein. In addition, database server 28 may include a conventional phone mail system with an associated database for storing voice mail messages. In this case, the data transaction may include voice data for storage in the remote voice mail system.

As shown in FIG. 1, several database servers 28 may be provided. Preferably, each transaction entry device 12 has an associated database server 28 for performing any desired processing of its data transactions, although it is preferred that the data transactions be copied to at least one other database server 28 as shown in FIG. 1. This redundancy minimizes the possibility of losing data in the event of a power outage and the like. Preferably, each database server 28 contains essentially the same hardware, although modem 32, transaction queue 34, and transaction controller 36 have not been shown for all database servers 28 for ease of illustration.

In transaction entry mode, the data transaction assembler 18 of transaction entry device 12 creates a data transaction that is transmitted to an associated transaction controller 36 of an associated database server 28. By "associated" it is meant that the database server 28 functions to perform any processing requested or necessary in conjunction with the storage of a data transaction from a particular transaction entry device 12. Of course, a particular database server 28 may have several transaction entry devices 12 associated with it. So that no data will be lost, a particular database server 28 may also serve as a backup for another database server 28 in the event of the failure of any database server 28.

As will be explained in more detail below with respect to FIGS. 2–4, database server 28 "explodes" data transactions received from data transaction assembler 18 and provides the component parts of the "exploded" file dependent data transactions via modem 32 to other database servers 28 as necessary to update other databases. Alternatively, as shown by dotted line in FIG. 1, the "explosion" of the data transactions may be performed by the data transaction assembler 18 at the transaction entry device 12 and the component parts transmitted to all appropriate databases 28 for updating the data therein. For this purpose, the data transaction assembler 18 will also need to know the modem numbers for all database servers 28 to be updated by the exploded data transactions. However, those skilled in the art will appreciate that this latter alternative will require access to numerous phone lines by the transaction entry device and that such phone lines are not always available to the user.

Finally, the third tier of the system 10 includes additional database servers 38 and databases 40 which support file dependent data transactions for specific applications. This additional tier of database servers 38 and databases 40 permits the data in the data transactions to be routed to application specific databases for storage of application specific data and access by those transaction entry devices 12 requesting data related to that specific application.

The creation and storage of a data transaction in accordance with the invention will now be described with respect to FIGS. 2–4.

Data transactions are created by data transaction assembler 18 as a data stream of a known format. A generic data transaction is illustrated in FIG. 2. As defined herein, a data transaction is created using a form containing one or more of the following: instructions, prompts, menu selection options, and a template with fields for data entry. Generally, the menu form consists of prompts for selecting a form, another menu, or a process, and a single slot for entering a selection, while the data entry form consists of prompts and instructions together with fields for entering data as shown in FIG. 2. The data entry form can have either single or multiple fields for entering data.

In transaction entry mode, the user navigates through menus of data transaction assembler 18 until a form related to a particular type of data entry operation is selected. Once selected, data transaction form 42 is presented to the user on display device 20. The data transaction form 42 is a collection of data defining the visual presentation on the display device 20 and a list of the fields through which linkages to external database files are defined.

Figure 2:
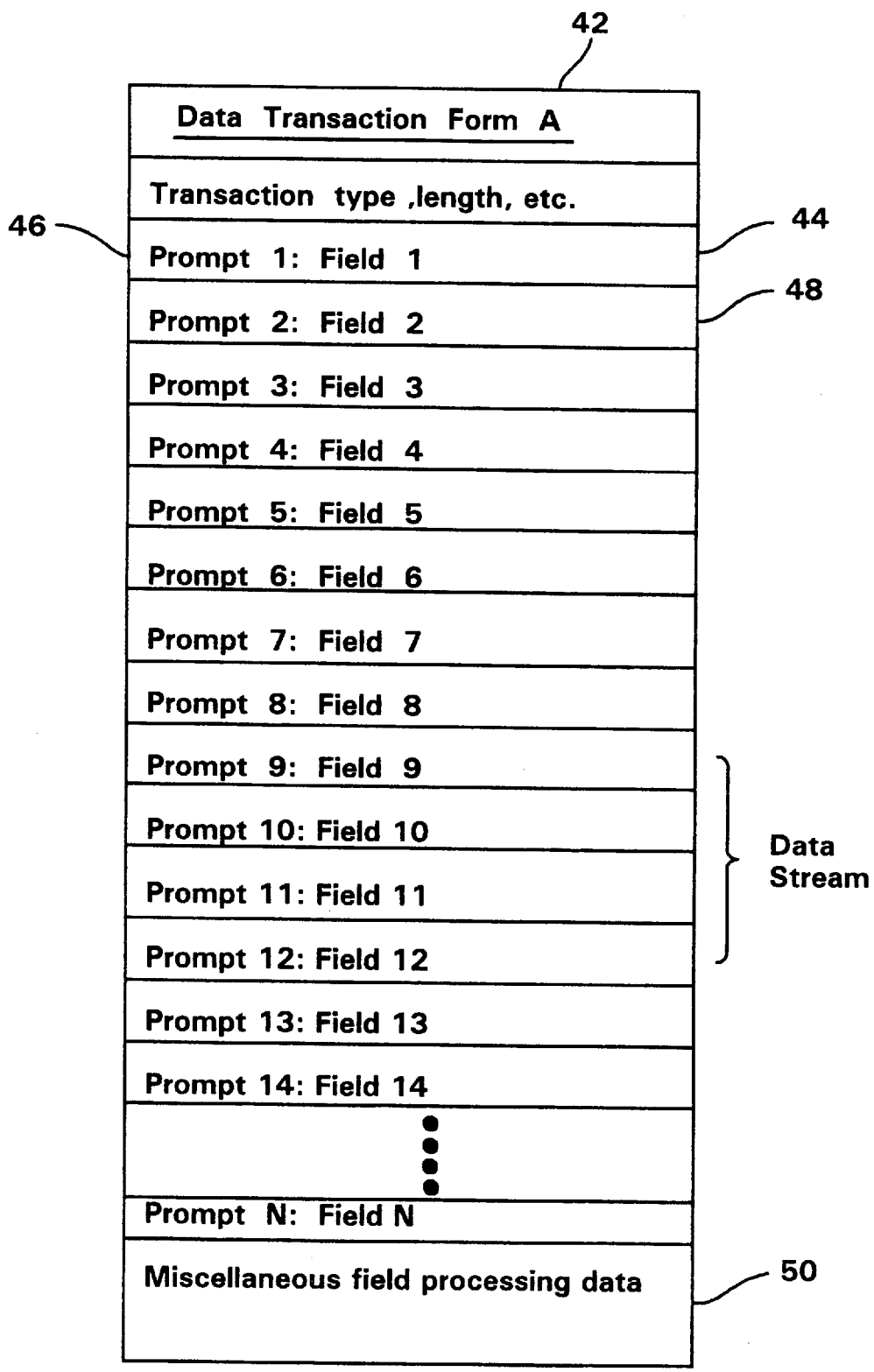
FIG. 2 illustrates a generic template for use in creating a data transaction in accordance with the invention.

As shown in FIG. 2, data transaction form 42 includes a format field 44 which identifies the type of data transaction this form pertains to, the length of the form, the number of pages in the form, the number of bytes in each field, storage keys, and the like. The body of the data transaction form 42 comprises a predetermined series of prompts 46 which are provided to the display screen 20 as a data stream. The prompts preferably include descriptive data which may be alphanumeric, an icon, or a list that scrolls, if necessary. Fields 48 are blank spaces of predetermined size provided for accepting user input in response to each prompt. Generally, the size of each field 48 is also stored in the stream of data defining the data transaction form 42. Since the prompts are tailored to elicit the necessary data for the application for which the data transaction form 42 was created, the fields 48 will include the user data necessary for processing a data transaction for that particular type of application. The user responses become part of the data stream which forms the data transaction. Typically, the data transaction form 42 also includes a miscellaneous processing field 50 which permits processing data unique to that form to be appended to the data transaction for transmission. Such processing data may include, for example, equations which define the relationships of the data in certain fields of the data transaction or audio or video data attached to a multimedia data transaction. In addition, non-display data associated with the time of data entry, the date of data entry, the user ID, and the like may be stored in miscellaneous processing field 50.

Figure 3:
FIG. 3 illustrates an "exploded" data transaction in which the component parts of a data transaction are stored in database-specific and file-specific locations.
Figure 4:
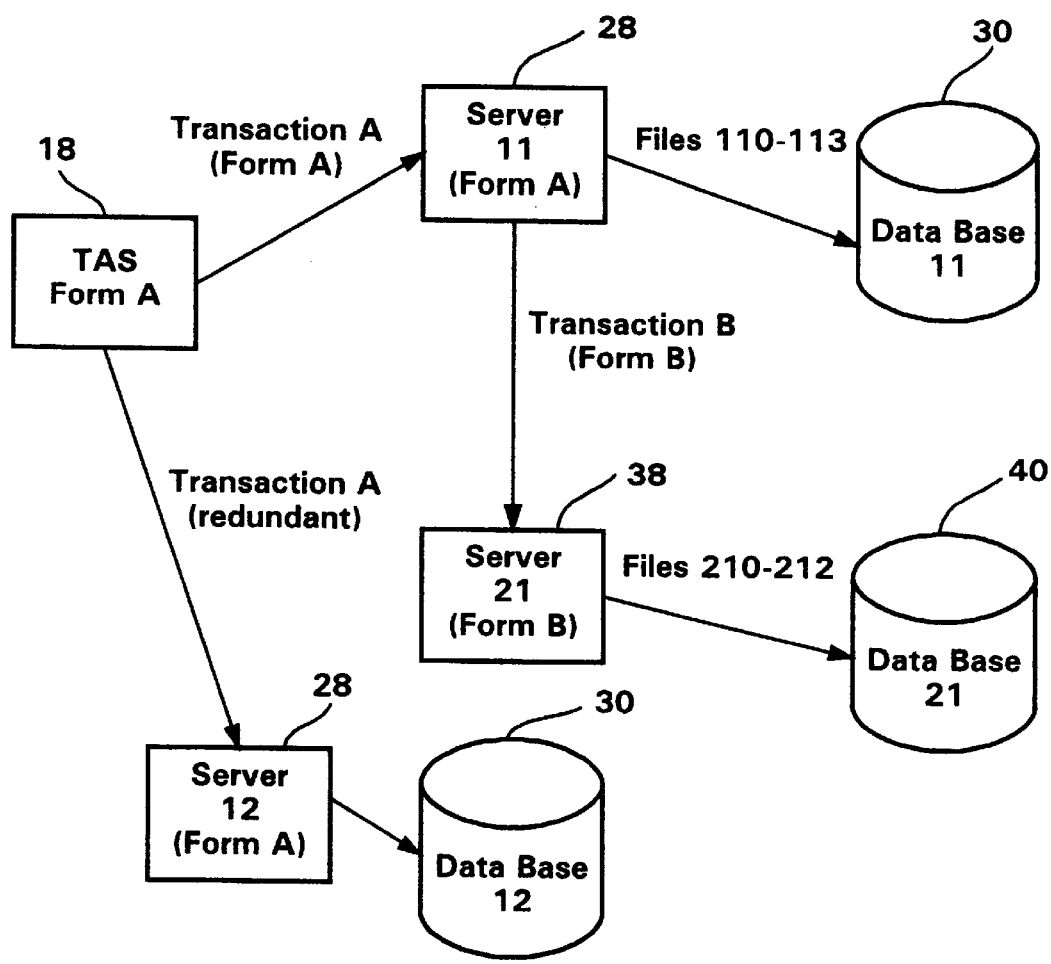
FIG. 4 illustrates the "exploded" transaction of FIG. 3 in the context of the system illustrated in FIG. 1.

FIGS. 3 and 4 illustrate the "explosion" of the stream of data forming the data transaction created using the data transaction form 42 of FIG. 2. As shown in FIG. 3, each data transaction contains data which is specific to a particular database and/or specific to particular files in one or more databases. The data in the data transaction is "exploded" accordingly. For example, the complete data transaction from FIG. 2 (Form A) is stored in a particular file (file 110) of the database associated with the transaction entry device 12 which created the data transaction (database 11 in FIG. 1). Storage of the entire data transaction is desired so that records may be maintained in the event of system error, power failure, and the like. The transaction controller 36 then extracts data from those fields of the data transaction which it knows to be related in forms of that particular type. For example, the data in fields 1, 2, 6, 10, and a function of the data in field 11 may relate to a particular application stored in file 111 of database 11. Similarly, the data in fields 3, 6, 10, 12, and 14 may be related to an application stored in file 112 of database 11, while the data in fields 1, 2, 7, 8, 9, and a function of the data in fields 10, 11, and 12 may be related to an application stored in file 113 of database 11. These fields are extracted from the received data transaction by transaction controller 36, reconstituted into a file entry of the appropriate format (as necessary), and stored in the associated database 30.

All of the data in the received data transaction, or a subset thereof, may also be retransmitted to one or more additional application specific databases, such as database 21 of the databases 40 in tier 3. As illustrated in FIG. 3, the database specific data of fields 1, 4, 5, 13, and 14, forming the subset (Form B) of the original transaction (Form A), is stored in file 210 of database 21 so that a complete record may be maintained. Subsets of the data in Form B are then stored in specific files of database 21 as indicated. In this manner, the data of the original data transaction (Form A) is automatically sent to all databases which contain files which must be updated by any or all of the data in Form A.

FIG. 4 illustrates the explosion of the data transaction in FIG. 3 for the system 10 illustrated in FIG. 1. As shown, the data in the data transaction (Form A) is extracted to update files 110–13 of database 11 as well as files 210–212 of database 21. A redundant copy of Form A is also maintained in database 12.

As will be explained more fully below, the system of FIGS. 1–4 is significant in that the data in a data transaction may update one or more databases serviced by file servers operating under control of numerous types of operating systems without the requirement of a terminal or operating system emulation by the transaction entry device 12. On the contrary, the transaction entry device 12 of the invention permits data capture and storage with a minimum amount of processing at the transaction entry point (tier 1), which, of course, minimizes system cost.

B. Transaction Entry Device 12 (FIGS. 5–10)

As noted above, the transaction entry device 12 is particularly characterized by the data transaction assembler 18, which controls the various operations of the transaction entry device 12 in its transaction entry mode. Preferably, data transaction assembler 18 uses simple menu structures and predetermined forms stored as data steams in a flash memory for facilitating data entry. The menus are treated as a special type of form and are used to call other menus, forms, or processes. The forms, on the other hand, are used to create data transactions which are sent to one or more file servers operating under different operating systems, where the data transaction is "exploded" into its component parts for storage in a unique file structure for updating all records affected by the data in that data transaction. In turn, the "exploded" data transactions may be transmitted to another application specific database (tier 3) for storage. Processes, on the other hand, are selected to perform limited processing of the values in the fields of the forms. Such processing may be performed locally but is preferably performed by the associated database server 28.

1. Hardware

Figure 5A:
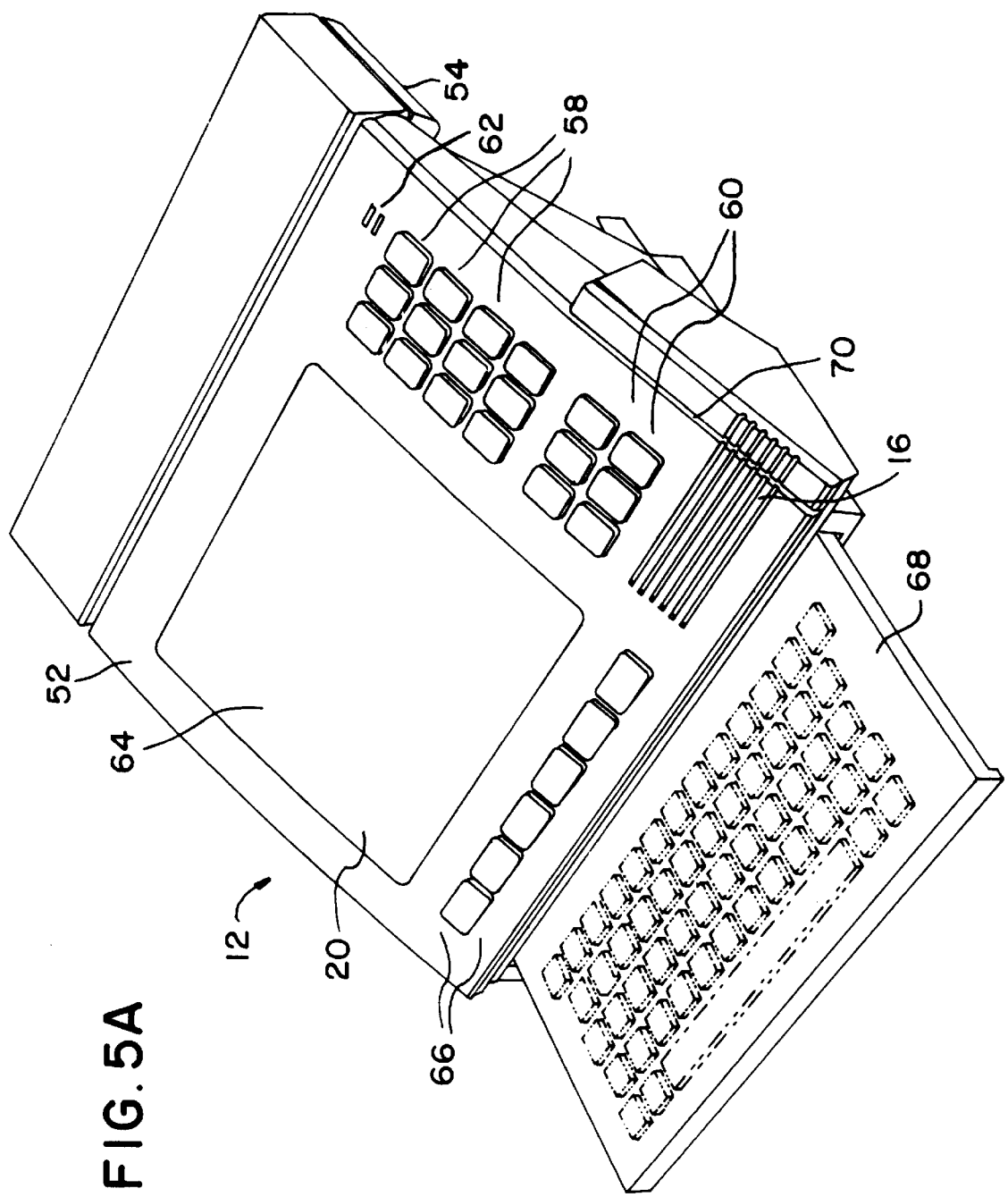
FIGS. 5(a) and 5(b) together illustrate a preferred embodiment of a transaction entry device in accordance with the invention.
Figure 5B:
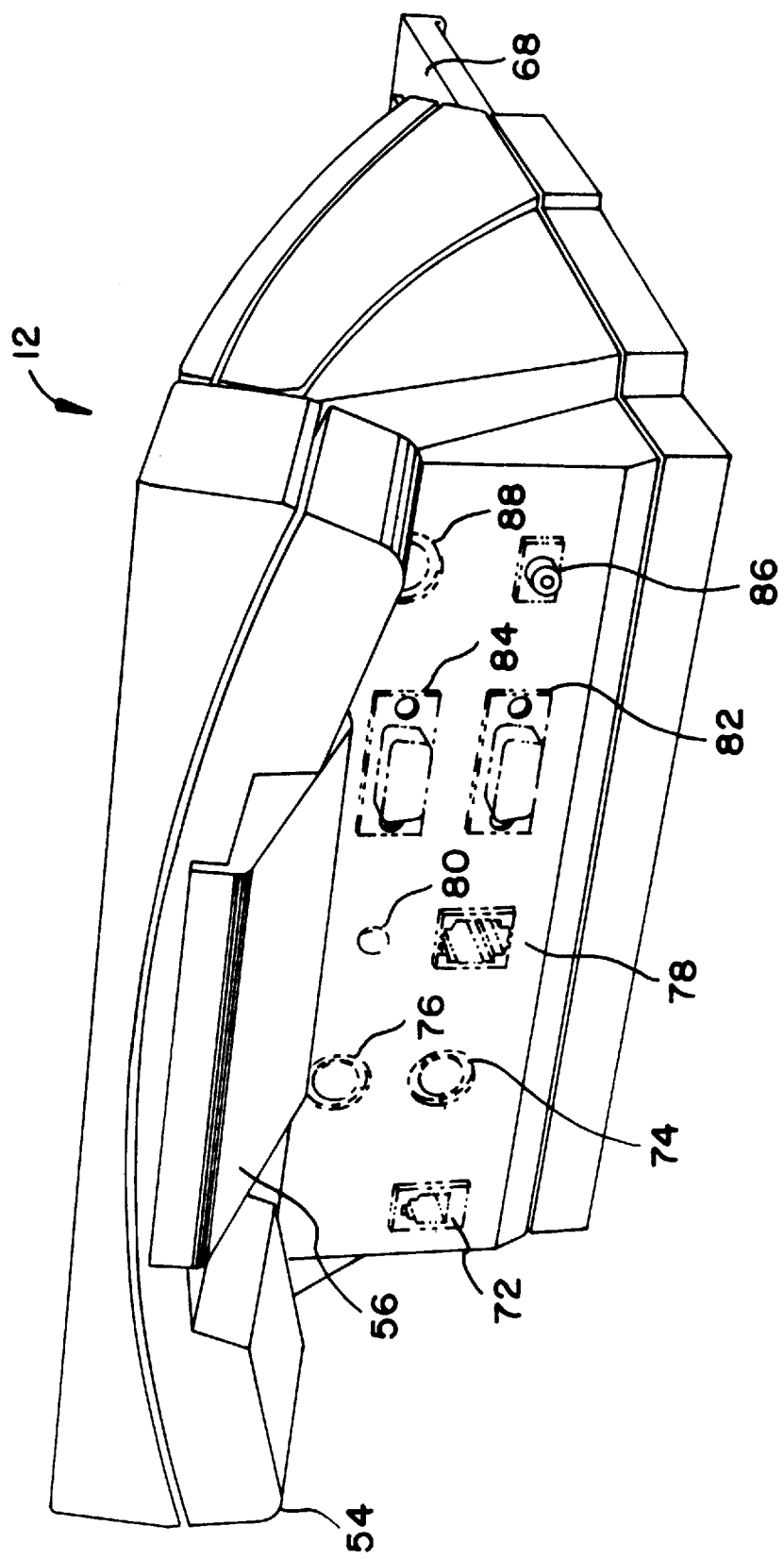
Figure 6:
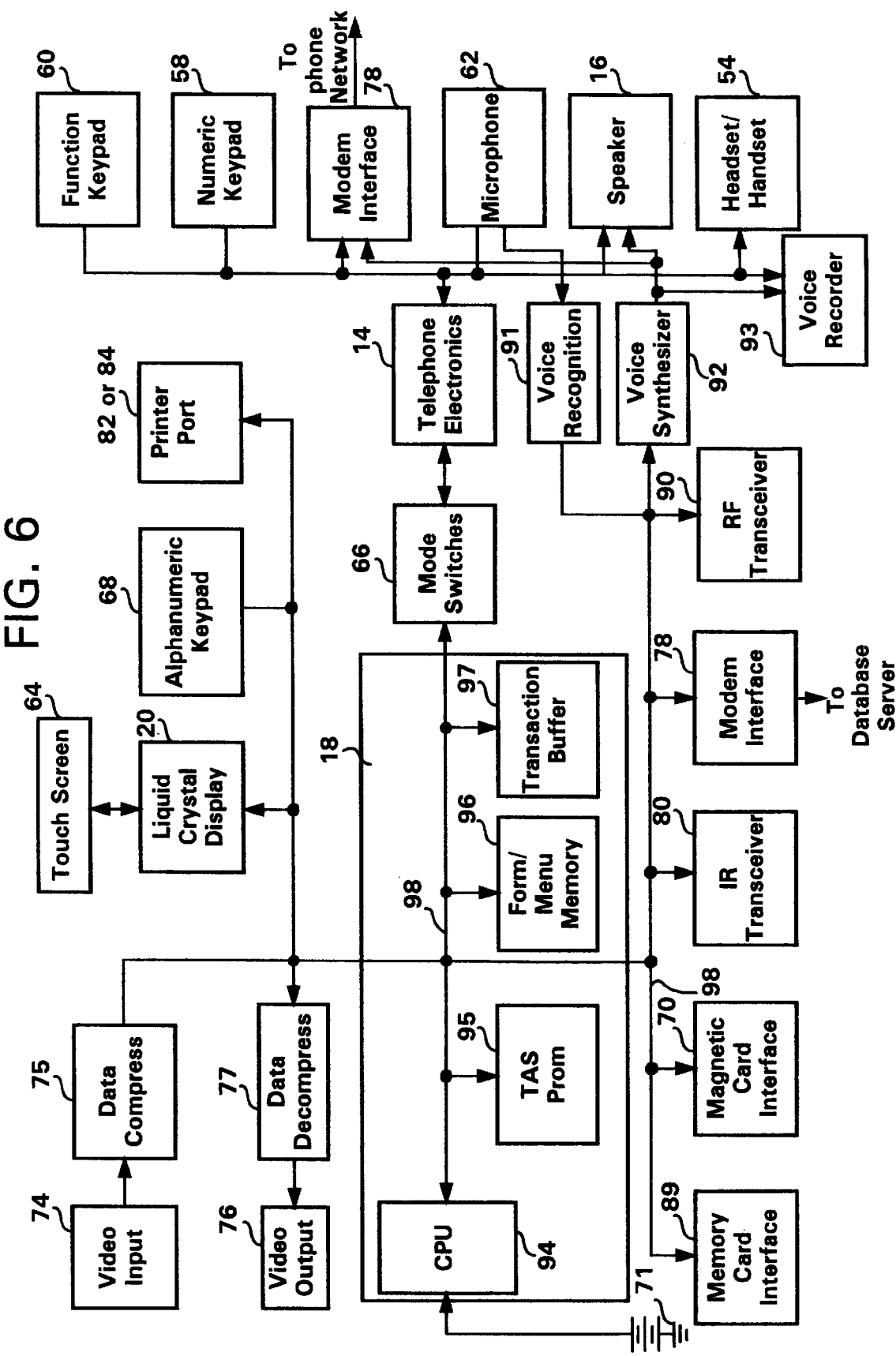
FIG. 6 is a schematic diagram of the electronics of the transaction entry device illustrated in FIGS. 5(a) and 5(b).

A preferred embodiment of a transaction entry device 12 incorporated into a conventional telephone is illustrated in FIGS. 5 and 6. As shown in FIG. 5a, a preferred desktop embodiment of a transaction entry device 12 includes a housing 52 on the order of 8 inches wide by 12 inches long for housing telephone electronics 14 and the hardware of data transaction assembler 18. Transaction entry device 12 includes an optional handset (or headset) 54, cradle 56 (FIG. 5b), numeric keypad 58, telephone function/line keys 60, microphone 62, and speaker 16, which facilitate operation of the transaction entry in the telephone mode. As known to those skilled in the art, telephone functions accessed by telephone function keys 60 may include mute, speaker, line select, conference, hold, transfer, volume control, and the like.

However, the transaction entry device 12 is further characterized by display 20 with touch screen 64, mode switch/computer function keys 66, optional retractable keyboard 68, and optional magnetic/smart card reader 70, which facilitate operation of the transaction entry device 12 in the transaction entry mode. A memory card reader may also be accessed via a door (not shown) as in a laptop computer. Preferably, display 20 is a super twisted, high contrast, reflective liquid crystal display (LCD) with a minimum of 20 characters per line and 16 lines (preferably, 40 columns by 24 lines), while touch screen 64 is preferably a clear pressure sensitive keyboard made up of 224 keys (16 rows of 14 keys) attached to the face of the LCD. Preferably, the LCD is also available as a backlit unit. Of course, touch screen 64 is not necessary if optional keyboard 68 is provided. In addition, a battery backup 71 (FIG. 6) may also be provided; alternatively, the battery 71 may be the primary power source for a portable (cellular) embodiment of the transaction entry device 12 in accordance with the invention.

FIG. 5b illustrates several of the connections to transaction entry device 12. Typically, transaction entry device 12 includes a handset (headset) jack 72 for connecting optional handset (headset) 54 to telephone electronics 14 when it is desired to communicate more privately than when only microphone 62 and speaker 16 are used. A video input port 74 is also provided for connecting conventional data compression circuitry 75 within the transaction entry device 12 (FIG. 6) to an optional video camera which provides picture phone type video or to a facsimile device or scanner. Such video data may be appended a frame at a time to the end of a data transaction in miscellaneous processing field 50 to create a multimedia data transaction as described above with respect to FIG. 2. A video output port 76 is also provided for providing decompressed video or facsimile data from video decompression circuit 77 (FIG. 6) to a video receiver, a high quality computer monitor, a facsimile device, and the like. Such data may also be provided to printer port 82 or 84 as desired. A multi-line phone jack (modem interface) 78 is also provided. Preferably, modem interface 78 provides separate modem connections for the telephone electronics 14 and the data transaction assembler 18, although only a single modem connection is necessary.

An optional infrared transceiver 80 is further provided for enabling remote control operation of television and stereo equipment and the like in response to data transactions transmitted/received by the transaction entry device 12. Infrared transceiver 80 includes an internal signal generator chip which reads parameters stored in data transaction assembler 18 for determining the appropriate transmission frequencies for the infrared signals. Control of the infrared devices is then provided through menus on the display 20. Additional infrared transceivers 80 may also be provided on each corner of the housing 52 so that the infrared signal will cover more area (each transmitter typically covers about 600 circumference). All such devices are known to those skilled in the art and thus will not be described in detail here.

A computer interface (RS-232) serial port 82 and parallel port 84 is also provided for transmitting/receiving data to/from another computer device and for providing output to a printer. A power input port 86 and a keyboard input 88 are also provided. Keyboard input 88 accepts a connection from a standard keyboard or a folding type keyboard (not shown) which may be used in addition to, or in place of, retractable keyboard 68. An optional removable PCMCIA memory card interface 89 (FIG. 6) for updating the operating instructions of the data transaction assembler 18 and an optional RF transceiver 90 (FIG. 6) for wireless networking to other electronic equipment may also be provided on the transaction entry device 12 as desired.

FIG. 6 is a schematic diagram of the electronics of the transaction entry device illustrated in FIGS. 5(*a*) and 5(*b*). Corresponding reference numerals for corresponding elements are used in FIGS. 5(*a*), 5(*b*) and 6. As shown in FIG. 6, in addition to the elements described above with respect to FIGS. 5(*a*) and 5(*b*), the transaction entry device 12 may include a simple voice recognition circuit 91 which permits voice selection of menu options and the like. In "voice selection" mode, the user would voice "1", "2" or "3" depending on the desired menu selection, and the voice would be picked up by microphone 62 on the housing 52 of the transaction entry device 12 and recognized by voice recognition circuitry 91. The proper selection signal would then be sent to the data transaction assembler 18. Similarly, the data transaction assembler 18 may provide audible output using a conventional voice synthesizer 92, which provides the audio output to the user via speaker 16 and to a caller via modem interface/telephone line connection 78. The voice synthesizer 92 may, for example, allow certain data transactions to be audibilized for a blind person who cannot make selections from a conventional video display. In addition, a voice recorder 93 may also be provided to record portions of telephone calls, portions of voiced data transactions, or a caller's message as when using a conventional digital answering machine. On the other hand, voice recorder 93 may be provided in database server 28 for use in storing/forwarding audible messages to the database 30.

As noted above, the transaction entry device 12 is characterized by data transaction assembler 18, which controls the creation of data transactions in the transaction entry mode. As shown in FIG. 6, data transaction assembler 18 is implemented in hardware using a conventional microprocessor 94, such as an Intel 80386SX (20 MHz or higher) or equivalent, a TAS PROM 95, a form/menu memory 96, and a transaction buffer (RAM) 97. In a preferred embodiment, TAS PROM 95 is a flash PROM which holds 1 MB of control data (firmware) for the microprocessor 94 (such as the microcode for the algorithms of FIGS. 7–10 below), while form/menu memory 96 is a flash memory which holds 1 MB of data transaction menus and forms. Transaction buffer 97, on the other hand, only needs to be as large as the largest data transaction, and may hold, for example, up to 128 kB of transaction data including application and operating system variables. Preferably, TAS PROM 95 and form/menu memory 96 are updated by downloading data streams containing new instructions and/or forms and menus over a conventional data bus 98 via modem 78, magnetic card interface 70, or via a removable memory card read by memory card interface 89 as necessary. Alternatively, additional flash memory elements may be added as additional applications are added to transaction entry device 12. Transaction buffer 97 may also be expanded to handle transactions of any size or type, including multimedia applications in which video and/or audio data is appended to data transactions.

Those skilled in the art will appreciate that the transaction entry device 12 may be docked into a docking station of a network. RF transceiver 90 may be used for wireless communications in such an environment. In addition, those skilled in the art will appreciate that the transaction entry device 12 may be implemented as a battery operated portable device which is a cross between a laptop computer and a cellular telephone of the type illustrated by Paajanen et al. in U.S. Pat. No. 5,189,632, for example. In such an embodiment, an optional headpiece could be provided, as well as a microphone and speaker arrangement in the fliptop. Of course, the liquid crystal display screen 20 would typically be reduced in size to, for example, 40 columns by 12 rows, and the touch screen 64 may be eliminated. However, most of the other options of the embodiment of FIGS. 5a and 5b would preferably remain so that the portable unit could also be used at a desk as desired. The electronics of the transaction entry device 12 would otherwise be as illustrated in FIG. 6 except for certain size and shape considerations well within the skill of those skilled in the art.

2. Software

As will be apparent from the following description, data transaction assembler 18 does not utilize a conventional operating system to control the operation of microprocessor 94. On the contrary, TAS PROM 95 stores simple firmware algorithms (FIGS. 7–10) operating in a kernel fashion for navigating a user through menus and forms provided from form/menu memory 96 for particular applications, and it is the resulting data streams which control the microprocessor 94 at any point in time. In other words, the data streams from the TAS PROM 95 and the data streams from the form/menu memory 96 together reconfigure microprocessor 94 into a special purpose processor for each application specified by the forms. The microcode of the TAS PROM 95 and the parameter streams from the form/menu memory 96 thus operate together as a simple form driven operating system for microprocessor 94 for all applications and is the sole code used to control microprocessor 94 (i.e., no conventional operating system or application programs are provided). As a result, the microprocessor 94 may be reconfigured into a new special purpose computer with each new form read from form/menu memory 96, and such forms/menus may be added at any time by reading in the appropriate data streams from a memory card or from an external database server 28 or by adding an additional PROM. A specific implementation of the TAS firmware stored in TAS PROM 95 will be described below with respect to FIGS. 7–10.

Thus, the TAS PROM 95 contains control data (firmware) for the microprocessor 94 and resides in each transaction entry device 12 for generating a template for a data transaction from a data stream stored in form/menu memory 96 (or received directly from a memory card or external database server) and from data input by a user or retrieved from an external database or magnetic card, smart card, and the like. The TAS firmware and the selected template together control the behavior of the microprocessor 94 by logically defining a table of menu options and/or database interfaces which are navigated through by the user. As noted above, the user navigates through a series of menu selections by selecting another menu, a form, or a process. Once the data transaction for a desired application is completed, it is transmitted out for "explosion" into all of its component parts for storage. In this form, the TAS firmware from TAS PROM 95 and menus and forms from form/menu memory 96 of the invention together replace a conventional operating system and individual application programs. Indeed, the invention permits the transaction entry device 12 to be completely operating system independent.

The data transaction assembler 18 of the invention is connected via a predetermined protocol stored as instructions within TAS PROM 95 to a database server 28 and its associated database 30. As noted above, the database server 28 associated with a particular transaction entry device 12 operates as a repository of the data transactions created by the transaction entry device 12 and as a supplier of data to the transaction entry device 12 for completing the forms and providing additional forms, menus, processes, and the like. Since the system of the invention is operating system independent, there are no hardware or software limitations on the characteristics of the database server 28.

The parameter set making up the individual forms are typically provided by database server 28 as a stream of data via modem and stored in form/menu memory 96, while any downloaded instructions are stored in TAS PROM 95. Linkage between data transaction assembler 18 and its database server 28 is preferably provided via a dictionary program specific to each database server 28. This dictionary program knows the characteristics of each field of each form for each data transaction and is used by the database server 28 to "explode" the received data transactions into their component parts.

Preferably, at power on, data transaction assembler 18 automatically prompts the user with a "Download Parameter Streams" command so that the user can load into form/menu memory (flash memory) 96 from an external source the desired streams of menu and form data for the desired application. The "download parameter" process will then be initiated by dialing the external database server 28 initiating the connection via the modem interface 78. Once connected, the transaction controller 36 of database server 28 will transmit the requested parameter stream. The data transaction assembler 18 will load the received data stream into form/menu memory 96, and, upon completion, the prompt "Executive Menu Ready" will be presented on the display screen 20. The executive menu then will be automatically presented to the user for selection of the desired menu, form, or process.

Upon initiation of the transaction entry mode by the user, data transaction assembler 18 calls a set of panel parameters from form/menu memory 96 and paints a form onto display screen 20. These forms are either menus for navigating to particular forms or a form into which data is entered by the user. As will be explained below, the menus provide functionality through simple menu selection. The form on the display screen 20 is completed by the user by entering the appropriate data using touch screen 64 or optional keyboard 68. Alternatively, the requested data may be read in from a memory card via memory card interface 90, from a magnetic strip on a swipe card or smart card via magnetic card interface 70 or memory card interface 89, or voice input via voice recognition circuit 91. In addition, a request may be sent to the database server 28 associated with the transaction entry device 12 for data needed to populate certain fields in the present form. The type of data entry is requested from a subset of options presented to the user upon pressing a "?" key or a "Request for More Information" button. This request will give the user several options to choose from, such as data entry using keyboard 68, touch screen 64, swipe card via magnetic card interface 70, memory card via memory card interface 89, by voice annunciation of the number of the item in the menu via voice recognition circuit 91, or via modem from a database 30. Hence, the data transaction created by the data transaction assembler 18 may or may not make use of stored data for reducing the amount of data entry required of the user.

When a data entry option is selected, data transaction assembler 18 does one of the following: another set of parameters is called up and another form is painted, the correctness of the selection is verified and a set of options for selections is presented based on interactions with stored data, the completed data transaction is transferred via modem to database server 28 for storage in database 30, or data values are requested from database 30 for incorporation within the transaction buffer 97. In a preferred embodiment, selections from the menu are made by touching the appropriate place on the menu using touch screen 64; by voice annunciation of the number of the menu item via microphone 62 and voice recognition circuit 91; by using one of the computer function keys 66 to run a cursor up the menu, another key to run the cursor down the menu, and a third key to make a selection in a conventional manner; or by using keyboard 68 as a selection device. When the keyboard 68 is used, the keyboard keys may be used to control a cursor, with the "enter" key being used for making a selection; alternatively, the number of the item selected may be entered and the "enter" key pressed to make the selection. Once the selection is made, the appropriate form is extracted from form/menu memory 96 as a stream of data.

Alternatively, in addition to presenting a menu for selection or completing a form, the data transaction assembler 18 can also present a menu selection for initiating a process such as calculation of an interest rate using one or more fields in the form, the finding of a mean, the finding of a name, or searching for entries for a particular date. These processes may be stored in TAS PROM 95, form/menu memory 96, in an off-line server where they are initiated, or any other place where they may be loaded down to the operating portion of the transaction entry device 12. In a preferred embodiment, processes are generally initiated in the database server 28 by sending a data request to the database server 28, processing the data in the database server 28, and then returning the answer as a data stream or report back to the transaction entry device 12.

A process typically initiates a data string which calls a process on an external machine. For example, the transaction entry device 12 may be used to download and store control signals for infrared control of various devices using infrared transceiver 80 (FIGS. 5 and 6). The form of the control signals will depend upon the signal storage in an optional infrared chip, which can be loaded by the data transaction assembler 18 or by an off-line device via modem or through the air using RF transceiver 90 for direct digital transfer in wireless form. In addition, in the case where the transaction entry device 12 is used in a medical office, for example, the process may be used to transmit a prescription to a pharmacy or mail order house using prestored modem numbers or may enable the physician to call up a list of phone calls to make for the day or a list of the followup appointments for a particular date. In other words, the TAS firmware can also "explode" the data transaction into all of its ancillary parts for transmission to numerous records in one or more databases.

A preferred embodiment of the TAS firmware will now be described with respect to FIGS. 7–10.

Figure 7:
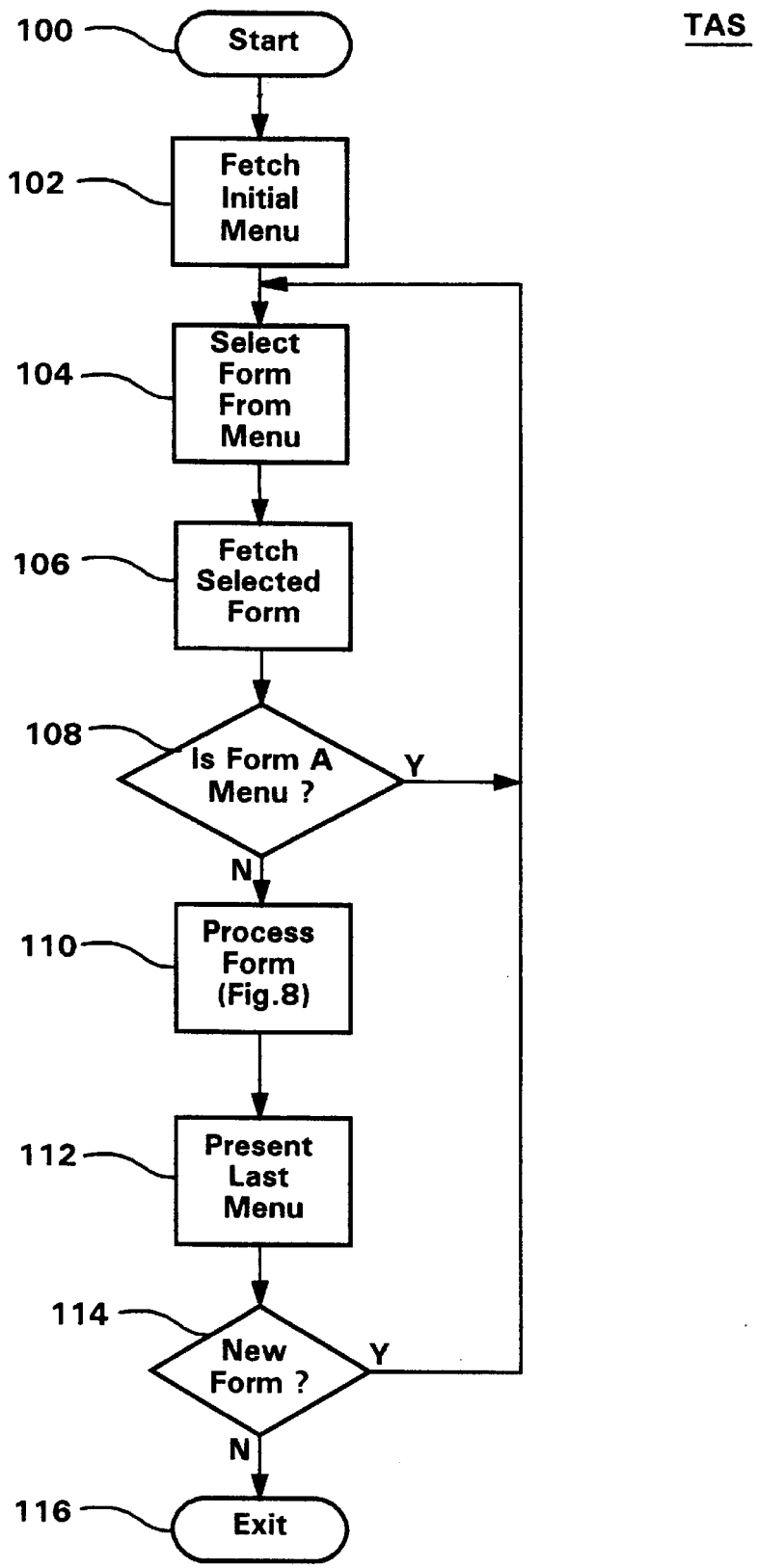
FIG. 7 is a flow diagram of a menu driven transaction assembly (application) server (TAS) in accordance with the invention.

As noted above, the transaction assembly (application) server (TAS) is a data stream stored in TAS PROM 95 which together with the forms from form/menu memory 96 create a simple form driven operating system which provides the necessary control data (firmware) to microprocessor 94 so that no conventional operating system is necessary. FIG. 7 is a flow diagram of a menu driven TAS in accordance with a preferred embodiment of the invention. As illustrated, the TAS firmware starts at step 100 and fetches an initial menu from form/menu memory 96 at step 102. The initial menu is prompted within a few seconds of booting the TAS firmware after the system logo. The initial menu typically presents the options of downloading a parameter stream from the database server 28 for enabling additional functions or printing an executive menu. If the executive menu is selected, the executive menu is retrieved from form/menu memory 96. The executive menu contains numerous application options to the user, namely, selection of a form, another menu, a process, or an automatic switch to telephone mode, one of which is selected at step 104. The data streams in form/menu memory 96 may be distinguished as to type (form, menu, or process) by appending a code such as "F" for form, "M" for menu, and "P" for process, and as to number by appending a form, menu, or process number at the beginning of the following data stream. These codes are recognized by the TAS firmware, and it acts accordingly.

If the option selected at step 104 is a form, the proper form (data stream for form $F_{xy}$) is fetched from form/menu memory 96 at step 106, a transaction buffer 97 equal in length to the size of the record associated with the form $F_{xy}$ is formed in RAM, the form is stored in the transaction buffer 97, and a connection is made to the appropriate database server(s) 28. The data stream for the selected form will consist of prompts, print locations for the prompt, data entry points, print locations for the data entry start, data entry length, and a code as to the nature of the data entry. This code can be numeric, alphanumeric, a cross-reference to stored data or previously entered data, a formula for the creation internally to data transaction assembler 18 of the result from previously entered data, or an external request for data, help, or reformulated values.

The data stream entered into the fields of the form will not only indicate the location for the printing of the prompt and the field for data entry, but also the size of the field and the storage, a start point within the transaction buffer for the stored element, and the type of data: alphanumeric, numeric (floating point or integer), date, and the like.

If it is determined at step 108 that the requested form is actually a menu ($M_{xy}$), a hidden set of codes pointing to the form $F_{xy}$ that the selection will lead to is read, and control branches back to step 104 for selection of another menu or form. When a menu is chosen, each item has its sequential number, its descriptor, and a code for what it will "call" (another menu, form, or process). In other words, each choice has associated with it a series of item codes which branch out to another form, menu, or series of tests upon the data entered. A menu also has a numeric code for each of the storage areas and a special code including a security code for certain menu items, process codes of forms within the menu, or a pointer to the process code. A pointer may also be provided in the menu for processes to be performed off-line (i.e., in an associated database server 28).

If a process ($P_{xy}$) is selected at step 104, the database server 28 is notified that something is requested from its database 30 or that some processing of data is requested. For example, the data transaction assembler 18 may send a user "?" inquiry to the database server 28 so that options may be returned to the data transaction assembler 18 for presentation to the user for selection. The process triggers an external process of database server 30 with a parameter stream, and control is either returned to the data transaction assembler 18 or control is held up until the process is complete, in which case a message is sent back to the data transaction assembler 18. This message can be a report, selected data, a value resulting from a calculation, and the like. Processing such as checking detectors and the like may also be performed locally by data transaction assembler 18.

Figure 8:
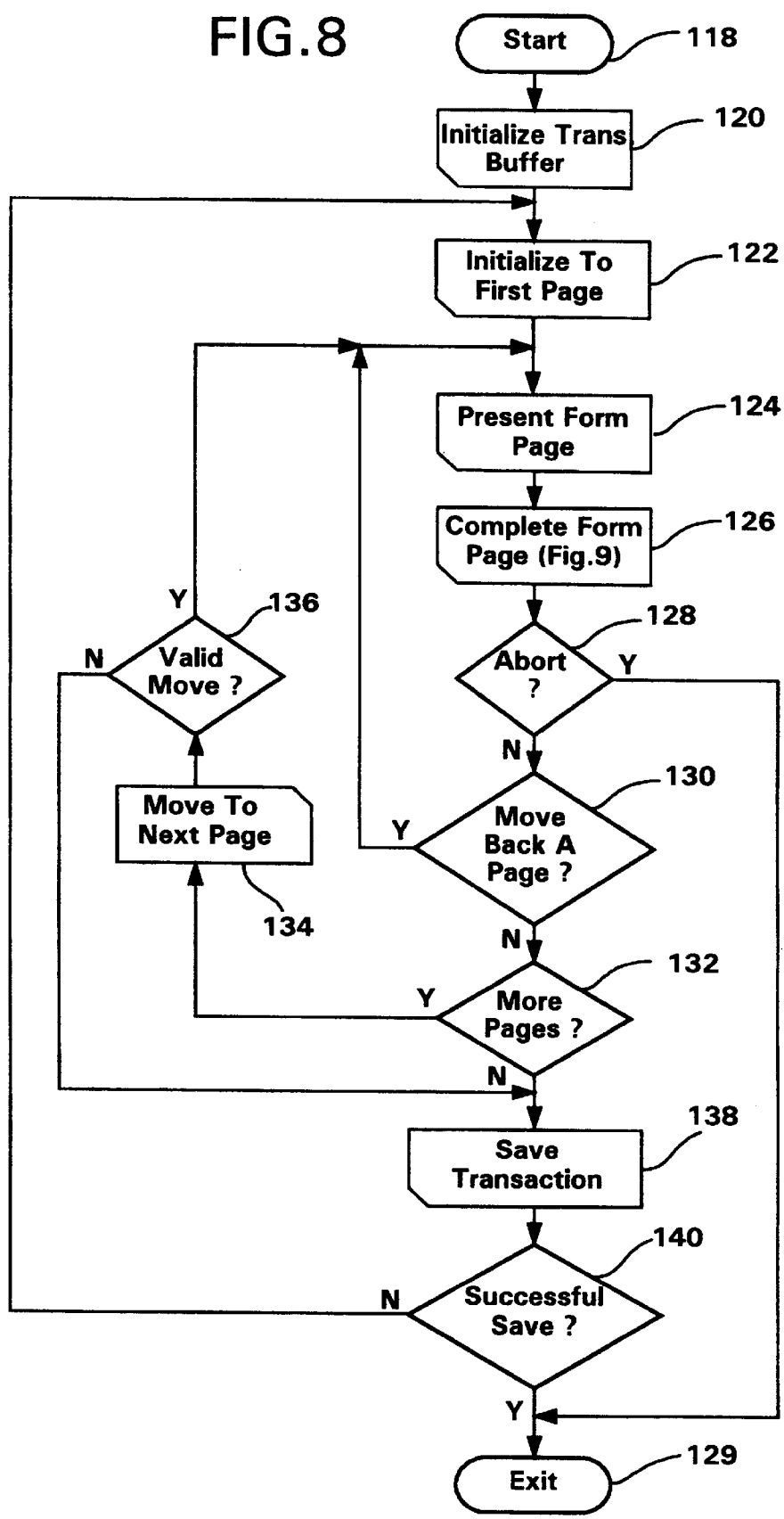
FIG. 8 is a flow diagram illustrating a technique for processing a form used to form a data transaction in accordance with the invention.
Figure 9A:
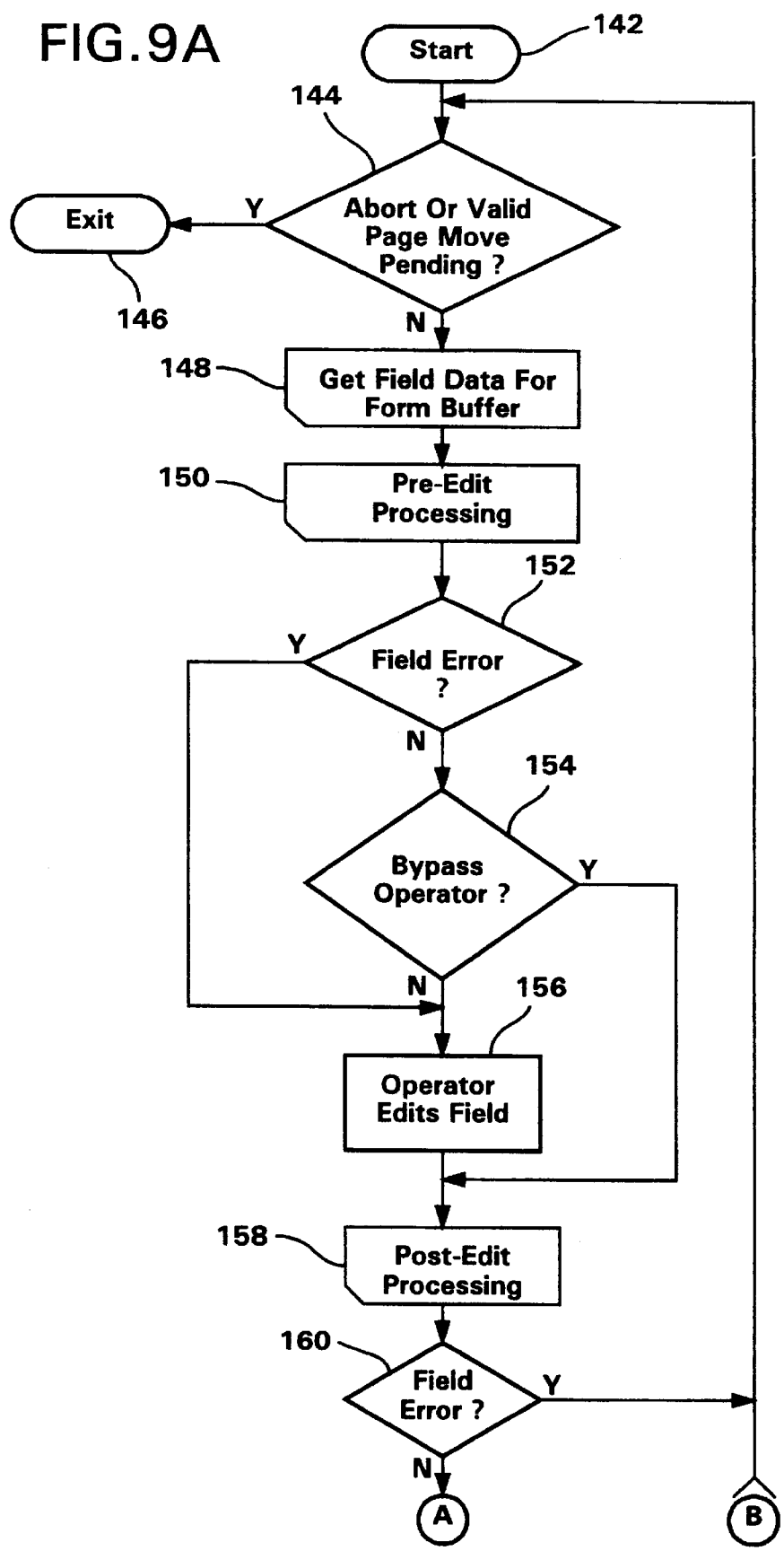
FIGS. 9(a) and 9(b) together illustrate a flow diagram of a technique for completing and editing a data transaction in accordance with the invention.
Figure 9B:
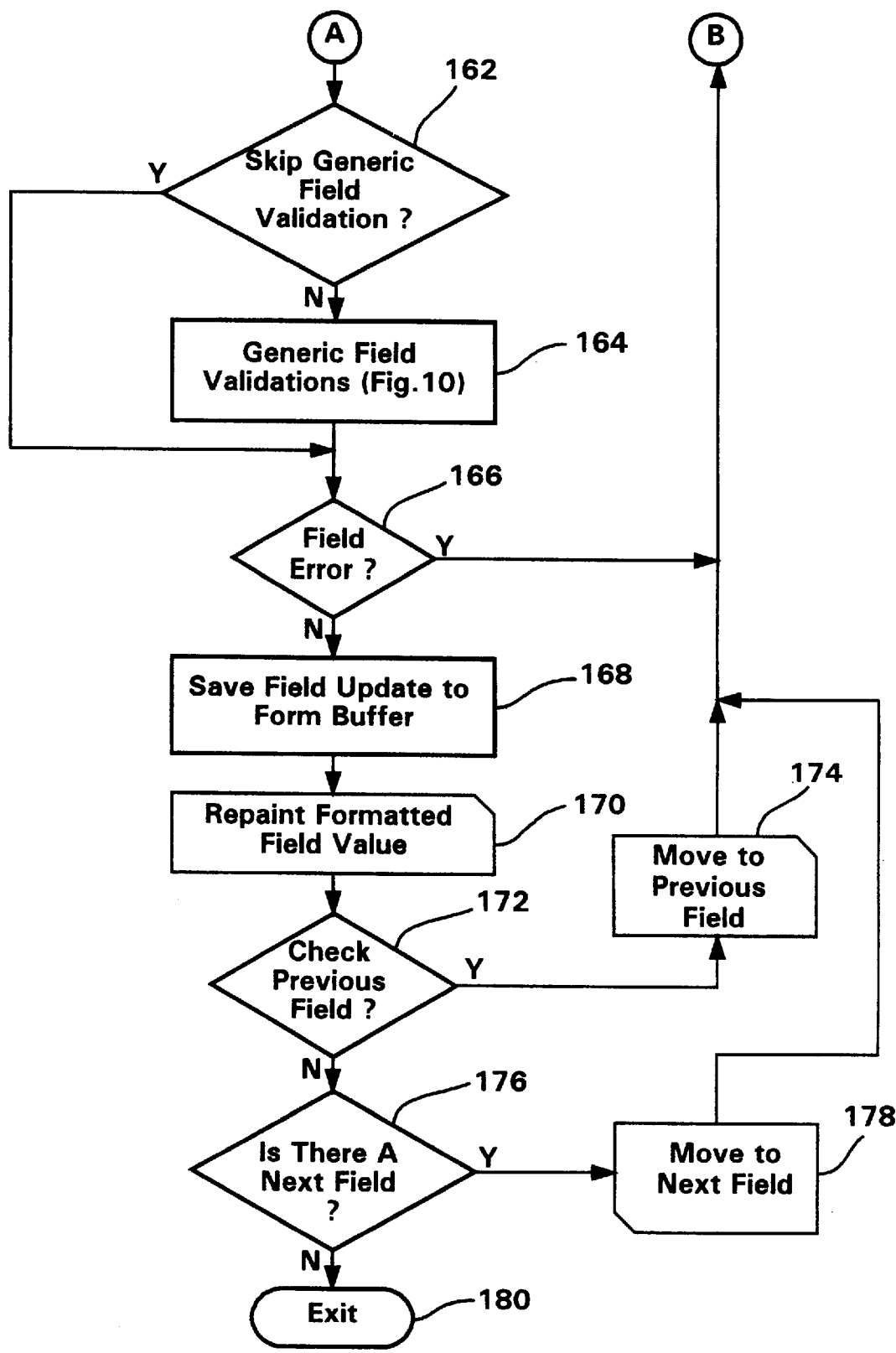
Figure 10:
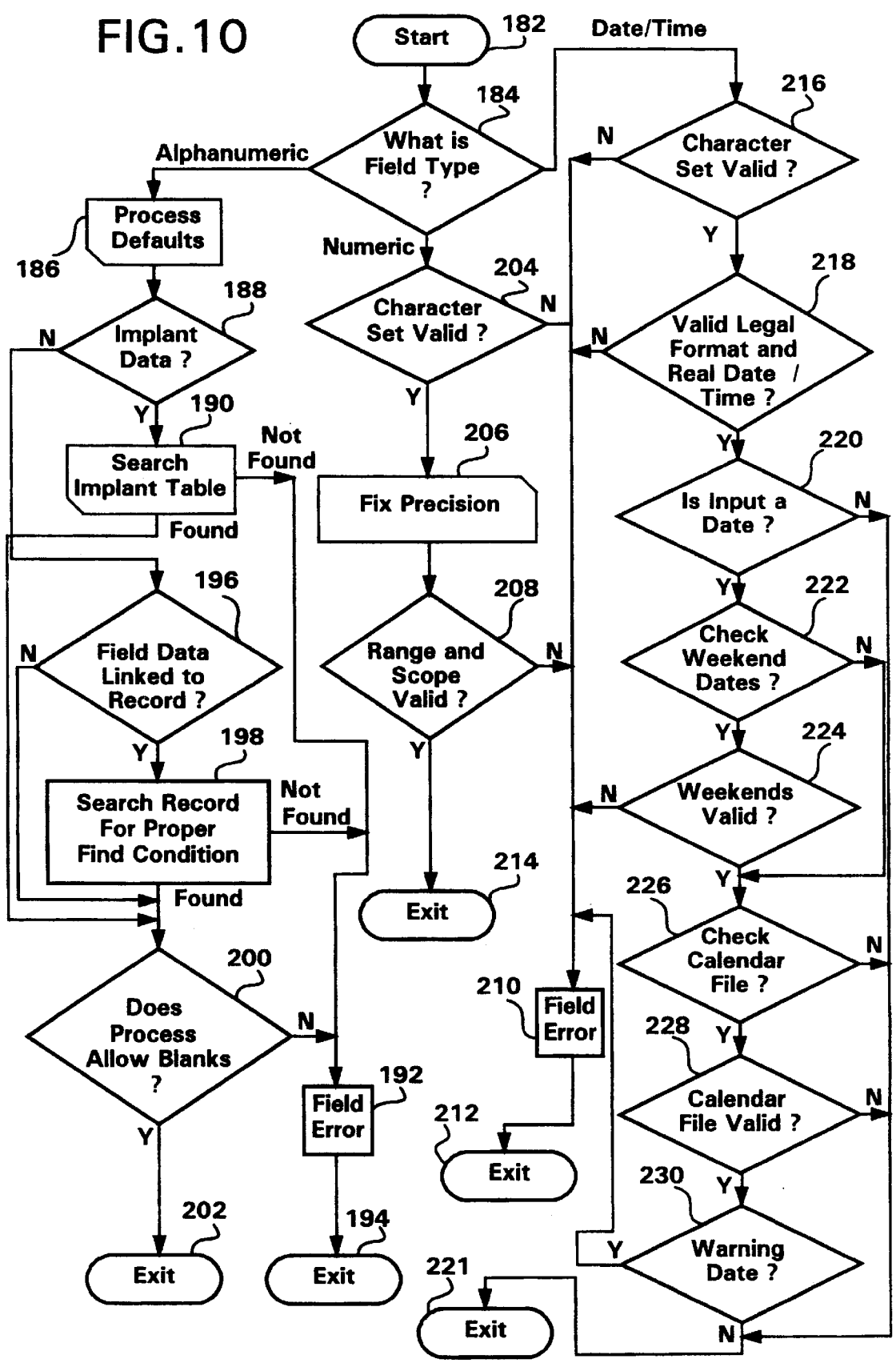
FIG. 10 is a flow diagram illustrating how the TAS validates the fields of each data transaction.

Once the desired form is selected for the user's application, the form is processed at step 110 in accordance with the steps outlined in FIGS. 8–10. As an entry is made in each field, it is automatically stored within the input buffer area of the transaction buffer 97 at its assigned location and in the dictated format. At any time, the entire form may be exited with automatic return to the menu which called it or the form can be cleared for data reentry. Once the form has been processed and transmitted to the appropriate database server(s) 28, the database server connection is terminated and the user is presented at step 112 with the last menu from which the user made his or her selection. Alternatively, the executive menu will be called up as a default menu.

If the user indicates at step 114 that he or she wishes to continue to complete a new form, control branches back to step 104 for menu selection and a new database server connection is made as appropriate. This process is repeated for each form. When no further selections are desired, the TAS firmware is exited at step 116.

FIG. 8 is a flow diagram illustrating a technique for processing a form (step 110) to create a data transaction in accordance with the invention. As illustrated, the process of FIG. 8 starts at step 118 and initializes a transaction buffer 97 at step 120 for storage of the data transaction as it is being created. In other words, if there is a form for the requested application, it is moved from form/menu memory 96 to the transaction buffer 97. If the requested form is not present in form/menu memory 96, an error message may be sent or a request may be sent to database server 28 for a download of a data stream containing the parameters for the requested form. Preferably, transaction buffer 97 is at least as large as the largest data transaction and serves as an assembly area for the data transaction. Preferably, read and write buffers are formed so that transmit and receive buffers to/from modem interface 78 are available. Of course, transaction buffer 97 may be made larger for this purpose.

Once the transaction buffer 97 is initialized at step 120, the display screen 20 is cleared and the selected form is initialized to its first page at step 122. The first page is then presented to the display screen 20 at step 124. At step 126, the user completes the form page on a field by field basis using any of the data entry techniques described above and the field controls of FIGS. 9 and 10.

The transaction buffer 97 collects the data associated with the form presented to the user on display screen 20 and contains appropriate locations for each separate data element. Upon completion of the data transaction, the contents of the transaction buffer 97 are transferred to the appropriate database server(s) 28 via modem or via wireless, preceded by a set of codes (field 44, FIG. 2) which identify the type of data transaction and followed by a string of process identifiers for the database server(s) 28 to use in its programs in creating additional transactions and in storing the data and all ancillary data transactions in the regular file format of the database 30 associated with the database server(s) 28. As a result, the data transaction created in the transaction buffer 97 has a one-to-many relationship to the data stored in the database 30.

If the user decides to abort the processing of a form at any time (step 128), the form processing routine is exited at step 129. Otherwise, it is determined at step 130 whether the user wishes to go back a page (for a multi-page form) to correct a data entry. If so, control returns to step 124 for presentation of the earlier page. If the user does not wish to examine or edit a previous page, it is determined at step 132 whether the current form has another page which has not been displayed for completion by the user. If the form has more pages, the routine moves to the next page at step 134, and it is determined at step 136 whether the move to the next page was successful. If so, control returns to step 124 for presentation of the next page. Of course, the process of calling a subsequent page in a form or another form upon completion of a form can be dependent upon an automatic call of that page or form sequence or the ability to jump sequence (i.e., skip pages) depending upon a value in any one field that has been entered. In any event, if there are no more pages in the form or if the move to the next page was not successful, the end of the form is marked with a code and the transaction is saved at step 138 by sending the data transaction to the appropriate database server(s) 28 for storage in its associated database 30 and "explosion" for storage of data in other databases 40. If it is determined at step 140 that the save was not successful because of a modem error and the like, control returns to step 122 and the process is repeated. If the data transaction was successfully saved, the form processing routine is exited at step 129 and the last menu used is presented (step 112).

Optionally, stored procedures within any data transaction form (field 50, FIG. 2) are executed at the appropriate time within the flow of the form processing routine before it is exited. However, these processes may be deferred and performed by the database server 28 if needed.

FIGS. 9(*a*) and 9(*b*) together illustrate a flow diagram of a technique for completing and editing the fields of a form (step 126 of FIG. 8). The field completion routine starts at step 142 and first determines at step 144 whether an abort or a valid page move request is pending. If so, the field completion routine is exited at step 146. However, if no abort or page move request is pending, the field data for the first field of the transaction buffer 97 is entered at step 148. As noted above, this field data may be entered via keyboard 68 or touch screen 64, swiped in via magnetic card interface 70, read in from a memory card via memory card interface 89, read in via modem interface 78 from database server 28, or designated by voice entry. Preedit processing of the field data is then performed at step 150. Such pre-edit processing may include, for example, setting default values, performing calculations, establishing links to data in other files, looking up and writing data to files already linked to the present form, spawning another form, performing special updates of the display screen 20, hiding fields from view by the user, and the like. Such pre-edit processing may also be used to determine whether modifications or actions in the present field may invalidate an entry in another interrelated field. If so, appropriate measures are taken to update all affected fields or to prevent such problems by setting appropriate default values.

The field completion routine then checks for field errors at step 152 on the basis of the default values and the like set at step 150. If there is no field error at step 152, it is determined at step 154 whether the operator will be permitted to edit the field in the absence of a field error. If so, or if a field error was found at step 152, the operator edits the field at step 156. If the operator editing is bypassed, control proceeds directly to post-edit processing at step 158, which performs essentially the same functions as pre-edit processing step 150 except that the data may be specially validated. The field is then checked yet again at step 160 for a field error. If a field error is found at step 160, control returns to step 144 for processing the next field or exiting, as appropriate.

If no field error is found at step 160, it is determined at step 162 whether the generic field validation routine of step 164 (FIG. 10) is to be skipped. If so, control proceeds to step 166, where the field is once again checked for a field error. However, if generic field validations are desired, control passes to the routine of step 164 (FIG. 10). If no field error is found at step 166, the field is saved to the transaction buffer 97 at step 168 and the updated field value is painted on the display screen 20 at step 170. If the user then desires to check a previous field at step 172, control passes to a previous field at step 174 and the field completion routine is repeated for the previous field. However, if no previous field is to be checked and if it is determined at step 176 that a further field is present, control passes to the next field at step 178 and the field completion routine is repeated for the next field. This process repeats until the last field is completed and the routine exits at step 180. Control then returns to FIG. 8 for processing a different page of the form.

Each form may be processed in one or more modes. In the input mode, described above, the data transaction is created and transmitted to the database server 28. However, in edit mode, upon entering the ID of a particular record, that record is read from an external database 30 or 40 into transaction buffer 97 for editing. Preferably, a record of the edits is maintained to provide an audit trail. In view mode, upon entering the ID of a particular record, that record is similarly read from an external database 30 or 40 into transaction buffer 97 but for display only. Finally, in delete mode, an entire record can be deleted from the database 30 or 40 if the user has proper security clearance.

FIG. 10 illustrates how the TAS firmware validates the fields of each data transaction. As shown, the field validation routine starts at step 182 and first determines at step 184 what field type is present. If the present field is an alphanumeric field, control passes to step 186 where the field defaults are processed. It is then determined at step 188 whether the user knows the values allowed for this field. If not, and data is to be implanted in that field, an implant table is searched at step 190. A "?" may be used by the operator to indicated that he or she does not know the values allowed for this field and wishes to search the implant table. A list of possible values are then called up that match the data entered thus far. From this list, the operator can scroll the list and select the value that will complete the data entry. However, if the value is not found in the list, a field error is generated at step 192 and the field validation routine is exited at step 194. If the value is found in the list, control passes to step 200.

On the other hand, if at step 188 it is determined that data need not be added (implanted) into the present field, control skips to step 196, where it is determined whether the present field type is a field which sets up an event in which the present field (along with its form) can be linked to any record of any file or files (one to many) of any database for the purpose of data verification and/or data extraction. If so, control passes to step 198, where the data from the present field along with any other data previously gathered is used to make the desired link. As in the data implant step 188 noted above, the user may enter a "?" to get the information needed to make this link. If the data for the link is not found, a field error is issued at step 192 and the field validation routine is exited at step 194. However, if the data for the link is found, the field is checked for blanks at step 200 and a field error is issued at step 192 if blanks are present in the field but are not allowed. If no blanks are found in the present field, or if blanks are found but are allowed, the field validation routine is exited at step 202.

If it is determined at step 184 that the present field is a numeric field, the field is checked at step 204 to determine if the character set is valid. If so, the precision of the numbers is adjusted at step 206, as necessary, and the range and scope of the numbers are checked at step 208 to make sure the field entries satisfy the boundary conditions (e.g., no dividing by zero). If the character set is not valid at step 204 or the range and scope of the numerals is not valid at step 208, a field error is issued at step 210 and the data validation routine is exited at step 212. Otherwise, the field validation routine is exited at step 214.

If it is determined at step 184 that the present field is a date/time field, the field is checked at step 216 to determine if the character set is valid. If not, a field error is issued at step 210 and the field validation routine is exited at step 212. Otherwise, a routine of the TAS firmware checks the date/time entry at step 218 to determine if it has the correct format by performing range checking and the like. If the date/time entry does not have the correct format, a field error is issued at step 210 and the field validation routine is exited at step 212. Otherwise, it is determined at step 220 whether the present field contains a date. If not, the data validation routine is exited at step 221. If so, the date is checked at step 222 to see if it contains a weekend, and, if so, checks at step 224 whether a weekend date is an acceptable reply for this field. It is then determined at step 226 whether the calendar file is to be checked, and if so, the calendar file is checked at step 228 to see if the date is valid (e.g., not a February 30 and the like). Finally, it is determined at step 230 whether a warning date has been exceeded, and if so, a field error is issued at step 210 before the field validation routine is exited at step 212. Otherwise, the field validation routine is exited at step 221.

Those skilled in the art will appreciate that, in order to maintain security, the TAS firmware may also present a security form for password entry to the user. The security form and ID of the transaction entry device 12 is then encrypted and transmitted to the database server 28 associated with the particular data transaction assembler 18. Transaction controller 36 of that database server 28 will then act as the transaction controller for that data transaction assembler 18 and will check passwords and the like during operation to make certain that data security is not breached. Database servers 28 may disable a data transaction assembler 18 if unauthorized use is attempted. In this manner, only the appropriate person may view each menu. Of course, a different number of security levels and different executive menus may be presented as desired, all under control of the transaction controller 36.

C. Database Server 28

As noted above, the database server 28 acts as a vehicle for separating data transactions created by the data transaction assembler 18 into the component parts thereof which may be stored directly in one or more databases 30 and 40. In other words, the database server 28 explodes the initial data transaction into data transactions for many different files for updating records in the files, and the like. Also, the database server 28 may be virtual as well as real, exist in a single machine or in multiple machines, in whole or in part.

Generally, the database server 28 handles any and all data transactions received, manipulates data in the data transactions, spawns or starts processes or reports requested by a data transaction, and explodes the received data transactions into all sorts of data transactions that were spawned by the initial data transaction. Database server 28 can also update values in existing records and can switch to a process for processing values in the records as necessary. In this manner, a single data transaction can define actions causing multiple files to be updated. Database server 30 also handles requests from the data transaction assembler 18 and processes them as needed. Such requests may include data I/O requests, data locking and unlocking, report processes, and requests for new forms or menus. Those skilled in the art will appreciate that database server 28 maintains the one-to-many relationships that exist between the user and the system of the invention, the one-to-many presentations to the user and files in the databases 30 and 40, and the one-to-many data transactions and the ancillary records, updates, and postings as may be required to diverse computer files of numerous databases 40, the transaction entry device 12 and the database servers 28.

As noted above, transaction buffer 97 collects the transaction data associated with the form presented to the user via display screen 20. The transaction buffer 97 is the image of the data transaction with appropriate locations for each separate data element. The contents of the transaction buffer 97 are transferred to the database server 28 via modem interface 78 or via RF transceiver 90, preceded by a set of codes 44 (FIG. 2) which identify the type of transaction followed by a string of process identifiers for the database server 28 to use in its programs, in creating additional data transactions, and in storing the data and all ancillary transactions within the database 30 in the regular file format of the database 30. In other words, the database server 28 determines what type of action to take based on the type of data transaction received, "explodes" a data transaction into a plurality of other data transactions for transmission to other databases, as appropriate, and converts the data for its associated database 30 into the proper file format. Of course, each database server 28 is different from each other database server 28 since it will handle different types of data transactions, have different operating system characteristics, and different file conversions to make in accordance with the file formats of its associated database 30. For example, the database server 28 may operate under an operating system such as Unix, Windows, or DOS, where the operating system provides the database server 28 with links to the hardware functions normally handled by an operating system. Preferably, the database server 28 also operates with menus, forms, and the like in the same fashion as the data transaction assembler 18 except that it stores the data transactions in its associated database 30 as transaction files.

As just noted, the purpose of the database server 28 is to process the data transaction from the data transaction assembler 18 and to either explode the data transaction into all of its related components for storage, to handle the storage of items from the explosion process, to store the data transaction itself for reference purposes, and to act as a supplier of information to the data transaction assembler 18 in response to requests during the creation of the data transaction and during the downloading of parameters for menus and forms to the data transaction assembler 18. If desired, the database server 28 can also supply information back to the data transaction assembler 18 after a data transaction is received or can initiate a process leading to the delivery of a report, data, or menu to the data transaction assembler 18. In addition, the database server 28 and data transaction assembler 18 can reside on the same machine so long as the database server's operating system recognizes the TAS firmware or the TAS firmware is modified for use with the operating system of the database server 28.

D. Applications of the Invention

As outlined above, the present invention includes a point of transaction device which presents a menu to a user from which an option is selected. A form tailored to the selected option appears for guiding the user through data entry. The full details of the data transaction are captured as data is entered by the user. Modem interaction with a central database(s) or a user database(s) allows for interaction for help and verification of certain entered data. The completed transaction is then transmitted to the central or user database for further processing and storage. Data input can also be provided via a swipe card or smart card, from data received from any database accessible via the modem interface, or other known methods.

A data transaction system of this type may be used for many applications. For example, in a first, presently preferred, application, the transaction entry device 12 is located in a medical office for entry of patient data. In this application, a swipe card identifies the patient, a smart card identifies the doctor, and the modem connection allows the entire claim transaction to be entered and transmitted to the insurance companies for processing. The patient records may also be automatically updated and prescriptions created, given to the patient, transmitted to the pharmacist, and transmitted to the payor and patient record. Patient instructions such as special diets, exercises, treatments, appointments, and the like may be printed from the data transaction form at the doctor's central computer. In addition, a video image or picture provided via video input 74 and compressed by data compression circuitry 75 permits an image of a medical condition such as a rash to be appended to the data transaction (in miscellaneous processing field 50 of FIG. 2) for transmission with the patient's name, the date, a description of patient symptoms, and the like. Similarly, a recorded heartbeat may be appended to the end of the data transaction for transmission with the patient data.

The data transaction entry system of the invention also has numerous home uses. In a preferred home use, the transaction entry device is used for performing bank transactions from the home. In this case, forms would be made available by the bank for different types of bank transactions. These forms would then be downloaded to the transaction entry device in the customer's home and used in creating and transmitting data transactions to the bank computer for off-line processing.

As another example, the user may dial-up to a 900 number to get an interface to a central database which will download codes into TAS PROM 95 or form/menu memory 96 which enable the generation of infrared signals at certain frequencies. The user needs only to specify the type, make and model of any electronic device to be controlled in order to get the desired code. Then, to operate any electronic device in the home, the user would be directed by menu prompts. The transaction entry device 12 would then emit an infrared signal via infrared transceivers 80 to operate the electronic device, initiate a call via modem for a broadcast program, or initiate timed requests for video recording, turning the video recorder on and off, and the like.

For other home uses, the transaction entry device 12 may also initiate, via menu prompts, sequences for turning on and off various household devices including alarm systems, coffeemakers, and the like. In this mode, the transaction entry device 12 may receive an RF or infrared signal indicating that a burglar or fire alarm has been activated and call up a form for calling the police or fire department, as appropriate. A call to the transaction entry device 12 may then be used to turn off the burglar or fire alarm by changing a field in a form which instructs the infrared transceiver 80 or RF transceiver 90 to send an appropriate control signal to the alarm device. This feature may also be prompted from a car phone via remote initiation of the form performing this function.

The transaction entry device 12 may also control all household telephone use as well as controlling the answering machine and keeping a telephone transaction log. The user may also pay household bills by completing an appropriate form and transmitting the form to a payee such as a credit card company, a bank, and the like. In short, the transaction entry device will permit the owner to connect to a remote database without owning a conventional computer system with an operating system and the like.

For personal applications, the transaction entry device 12 may be used to initiate a facsimile transmission, to provide telephone lists with automatic dialing upon selection, to provide expense accounts, personal scheduling, tax record keeping, and the like, and to provide direct access to travel information. For example, the database server 28 may be an airline reservations system. In this application, the data transaction assembler 18 dials the modem of the airline reservations system when the user requests data entry into an airline reservations form available at the user's transaction entry device 12. The data transaction device 18 modems the database server 28, and the operating system of the database server 28 selects interface programs for the airline reservations system. The interface programs call the database servers 38 of the airlines, retrieve the appropriate menu from database 40, and modem the menu to the data transaction assembler 18. The data transaction assembler 18 then displays the airline reservations menu on its display screen 20 for completion and transmission back to the airline reservations database server for processing. The swipe card may be used to provide credit card payment information and may be updated by permitting the data transaction assembler 18 to write to the swipe card. The user may also access frequent flyer club and mileage data, special offers on hotels, cruises and other travel, and the like.

In another home (or business) use, the transaction entry device 12 may be used to eliminate conventional phone mail greetings by enabling the caller's transaction entry device 12 to read in a set of visible menus from the called party's voice mail menu so that the calling party may select the desired options using a visible menu rather than a voiced menu. In other words, the caller would not have to wait through the litany of voiced phone mail options before making a selection and could make the desired selection right off of his or her own display. This would be accomplished by selecting a process from the menu of the transaction entry device 12 which will create a "visible" menu. When such a process is selected, the telephone electronics 14 or modem interface 78 makes a telephone connection to a remote phone mail system. Once the connection is made, the data transaction assembler 18 sends a data request for a visual representation of the phone mail menu of the remote phone mail system via the telephone connection to the remote phone mail system. A data stream containing the visual representation of the phone mail menu from the remote phone mail system is then returned via the telephone connection and stored in form/menu memory 96 and presented to display screen 20 of the transaction entry device 12 for selection using the techniques described herein. When menu items are selected from the "visible" voice mail menu, the data transaction assembler 18 creates a data transaction indicating which menu item was selected and sends the data transaction to the remote phone mail system via the telephone connection. Based on the menu selection, the remote phone mail system then returns a data stream containing a visual representation of the next phone mail menu via the telephone connection for storage in form/menu memory 96 and display on display screen 20. This process is repeated until the calling party is required to leave a message or the called party is reached. Such a system would be particularly helpful for interacting with voice mail systems, such as those at government offices, where numerous options are presented for selection.

Those skilled in the art will appreciate that the invention is unique by virtue of its ability to generalize applications to forms so that no code need to be written to implement a particular function. However, if code is needed or if multimedia data is to be part of a data transaction, it can be attached to a form which is stored as a parameter stream in a stream of data. Also, though the transaction entry device 12 has been described as a computer workstation, it can also be used in conjunction with an optional off-line storage device as a self-contained workstation and database unit independent of traditional operating systems. The transaction entry device 12 can also be used with an additional optional plug in as a network server or as a user interface in a network docking station.

Those skilled in the art will also appreciate that the foregoing has set forth the presently preferred embodiments of the invention but that numerous alternative embodiments are possible without departing from the novel teachings and advantages of the invention. Accordingly, all such modifications are intended to be included within the scope of the appended claims.

I claim:

1. A system for entering transaction data into a remote database, comprising:

a data input device;

a display;

a data transaction terminal including a microprocessor, a form memory which stores a plurality of menus and forms for presentation to a user, and a form driven operating system which controls a process implemented by said microprocessor to present to said display for each process at least one form stored in said form memory as data streams, said at least one form being selected by said user from one of said menus using said data input device, said one menu providing said user with an option of selecting at least one of said at least one form, another menu, and an updating process, each form eliciting data input of a desired transaction type into said data input device by said user and including at least one prompt customized to said desired transaction type, wherein said process implemented by said microprocessor is changed by changing said at least one form, and wherein when said user selects said updating process from said menu, data streams are downloaded to said form memory to update said menus and forms in accordance with said desired transaction type, said data transaction terminal further including means for formatting at least said data input by said user in response to said at least one prompt into a data transaction for transmission to said remote database; and a database server associated with said remote database which receives said data transaction, creates from said data transaction, depending on said desired transaction type, at least one additional data transaction containing data for a particular record in said remote database, and stores said at least one additional data transaction in said particular record.

2. A system as in claim 1, further comprising a plurality of remote databases, wherein said database server further creates from said data transaction, depending on said desired transaction type, at least one ancillary data transaction containing data for a particular record in one of said plurality of remote databases besides said remote database and stores said at least one ancillary data transaction in said particular record.

3. A system as in claim 2, wherein said form driven operating system includes means for sending a data request to said database server, said database server accessing data corresponding to said data request in at least one of said remote databases and returning one of data responsive to said data request, a list of options for selection by said user, a value calculated from data contained in said data request, and a data report.

4. A system as in claim 1, wherein said form driven operating system comprises a transaction assembly server (TAS) which presents said data streams to said microprocessor for display on said display, and said formatting means comprises a transaction buffer which stores said data input into said data input device by said user in response to said at least one prompt until said data transaction is completed for transmission to said remote database.

5. A system as in claim 4, wherein said data transaction terminal further comprises a modem, a telephone and two telephone line connections, one for connecting said telephone to a telephone network, and one for providing a modem connection among said modem, said TAS, and said database server.

6. A system as in claim 5, wherein said data transaction terminal further comprises a mode switch for selecting a telephone mode in which said data transaction terminal operates exclusive of said TAS or a transaction entry mode in which said TAS operates exclusive of said telephone.

7. A system as in claim 4, wherein said data transaction terminal further comprises a modem, a telephone, a telephone line connection, and means for selectively connecting said telephone to a telephone network and said TAS to said database server via said telephone line connection.

8. A system as in claim 7, wherein said selectively connecting means comprises a mode switch for selecting a telephone mode in which said data transaction terminal operates exclusive of said TAS or a transaction entry mode in which said TAS operates exclusive of said telephone.

9. A system as in claim 1, wherein said database server comprises a modem, a data transaction queue for storing data transactions received from said data transaction terminal, and a transaction controller which processes the received data transactions to extract physical relationships of data of said data transactions with records in said remote database.

10. A system as in claim 1, wherein said one menu further contains a remote process option, and when said user selects said remote process option from said one menu, data streams are downloaded via a modem to said form memory, said data streams containing control data for implementing functions designated by said selected remote process option.

11. A system as in claim 10, wherein said data transaction terminal further comprises an infrared transceiver and said control data comprises data for controlling a wavelength of energy emitted by said infrared transceiver.

12. A system as in claim 10, wherein said data transaction terminal further comprises a phone list memory for storing a phone list and said control data comprises data for updating said phone list.

13. A system for entering transaction data into a plurality of remote databases, comprising:

a data transaction terminal for capturing a data transaction having a one-to-many relationship to records of said plurality of remote databases, said data transaction terminal including a microprocessor, a form memory which stores a plurality of menus and forms for presentation to a user, and a form driven operating system which controls a process implemented by said microprocessor to present to said user for each process at least one form stored in said form memory as data streams, said at least one form eliciting data input of a desired transaction type into said data transaction terminal by said user, said data streams of said at least one form including at least one prompt customized to said desired transaction type, a format field which identifies said desired transaction type of said at least one form, a data entry field including said at least one prompt and spaces for said data input by said user in response to said at least one prompt, and a processing field for appending data particular to said desired transaction type, said data transaction terminal further including means for formatting at least said data input by said user in response to said at least one prompt into said data transaction for transmission to at least one of said plurality of remote databases;

a first set of database servers associated with a first set of remote databases of said plurality of remote databases, said first set of database servers receiving said data transaction, creating from said data transaction a plurality of ancillary data transactions having a one-to-one relationship to said records of said plurality of remote databases, and storing said ancillary data transactions in designated records of said first set of remote databases; and a second set of database servers associated with a second set of remote databases of said plurality of remote databases, said second set of database servers receiving certain of said plurality of ancillary data transactions, and creating from said certain ancillary data transactions additional data transactions which are stored in application specific records of said second set of remote databases in accordance with said desired transaction type of said at least one form.

14. A system as in claim 13, wherein each database server of said first and second set of database servers comprises a modem, a data transaction queue for storing data transactions, and a transaction controller which processes a received data transaction to extract physical relationships of data of said data transactions with records of a remote database associated with said each database server.

15. A system as in claim 13, wherein said data particular to said desired transaction type includes at least one of audio and video data.

16. A data transaction terminal for providing data transactions to a remote database server which stores records in an associated database, comprising:

a data input device;

a display;

a telephone circuit;

a data transaction assembler including a microprocessor, a form memory which stores a plurality of menus and forms for presentation to a user, and a transaction assembly server (TAS) which controls a process implemented by said microprocessor to present to said display for each process at least one form stored in said form memory as data streams, said at least one form being selected by said user from one of said menus using said data input device, said one menu providing said user with an option of selecting at least one of said at least one form, another menu, and an updating process, each form eliciting data input of a desired transaction type into said data transaction assembler by said user and including at least one prompt customized to said desired transaction type, wherein said process implemented by said microprocessor is changed by changing said at least one form, and wherein when said user selects said updating process from said menu, data streams are downloaded to said form memory to update said menus and forms in accordance with said desired transaction type, and means for formatting at least said data input by said user in response to said at least one prompt into a data transaction for transmission to said remote database server; and a mode switch for selectively connecting said telephone circuit to a telephone network in a telephone mode and said data transaction assembler to said remote database server in a data transaction entry mode.

17. A terminal as in claim 16, wherein said formatting means comprises a transaction buffer which stores said data input into said data input device by said user in response to said at least one prompt until said data transaction is completed for transmission to said remote database.

18. A terminal as in claim 16, further comprising a modem and two telephone line connections, one for connecting said telephone circuit to said telephone network, and one for providing a modem connection among said modem, said TAS, and said remote database server.

19. A terminal as in claim 16, further comprising a modem and a telephone line connection, said mode switch selectively connecting said telephone and said TAS to said telephone line connection.

20. A terminal as in claim 16, wherein said one menu further contains a remote process option, and when said user selects said remote process option from said one menu, data streams are downloaded via a modem to said form memory, said data streams containing control data for implementing functions designated by said selected remote process option.

21. A terminal as in claim 20, further comprising an infrared transceiver, said control data comprising data for controlling a wavelength of energy emitted by said infrared transceiver.

22. A terminal as in claim 20, further comprising a phone list memory for storing a phone list, said control data comprising data for updating said phone list.

23. A terminal as in claim 17, wherein said TAS presents one of said menus to said user for selection, said one menu containing pointers to a plurality of forms, and upon selection of said at least one form from said menu by said user, said TAS initializes said transaction buffer and presents said at least one form to said display on a page by page basis for entry of said input data by said user.

24. A terminal as in claim 16, wherein said TAS processes said input data as it is entered in response to each prompt to determine if said input data satisfies predetermined conditions for input data entered in response to each said prompt.

25. A terminal as in claim 16, wherein said TAS sends a data request to said remote database server when said user requests assistance in replying to a prompt and inserts reply data from said remote database server into said data transaction in response to said prompt.

26. A terminal as in claim 16, wherein said TAS comprises means for creating from said data transaction, depending on said desired transaction type, at least one ancillary data transaction containing data for a particular record in said associated database and storing said at least one ancillary data transaction in said particular record in said associated database.

27. A terminal as in claim 26, wherein said ancillary data transaction creating means further creates from said data transaction, depending on said desired transaction type, an ancillary data transaction containing data for an application specific record in a secondary database and sends said ancillary data transaction to said secondary database for storage of said ancillary data transaction in said application specific record.

28. A terminal as in claim 16, wherein said data transaction assembler includes means for sending a data request to said remote database server, said remote database server accessing data corresponding to said request in said associated database and returning one of data responsive to said request, a list of options for selection by said user, a value calculated from data contained in said data request, and a data report.

29. A terminal as in claim 16, wherein said data input device comprises at least one of a touch screen associated with said display, a telephone numeric keypad, an alphanumeric keyboard, a memory card reader, and a magnetic card reader.

30. A terminal as in claim 29, wherein said alphanumeric keyboard comprises a retractable keyboard which retracts into a housing of said data transaction terminal.

31. A terminal as in claim 16, further comprising a video input terminal for receiving input video data and a video output terminal for providing output video data to a video monitor.

32. A terminal as in claim 31, further comprising a data compression circuit for compressing said input video data prior to including said input video data in a data transaction and a data decompression circuit for decompressing output video data prior to display on said video monitor.

33. A terminal as in claim 16, further comprising a computer I/O port for receiving input data from a computer device and providing output data to at least one of said computer device and a printer.

34. A terminal as in claim 16, further comprising a RF transceiver for providing a wireless connection between said data transaction terminal and a data processing device.

35. A terminal as in claim 16, further comprising a battery for providing power to said data transaction terminal for portable operation.

36. A terminal as in claim 16, wherein said data input device comprises a voice recognition circuit for accepting data input selections annunciated by said user.

37. A terminal as in claim 16, further comprising a voice synthesizer responsive to said data transaction for audibilizing a portion of said data transaction to said user.

38. A terminal as in claim 37, further comprising a voice recorder for recording at least one of said audibilized portion of said data transaction when in said data transaction entry mode and voice input from a called party when in said telephone mode.

39. A method of entering transaction data into a remote database using a data transaction terminal, comprising the steps of:

storing a plurality of menus and forms in a form memory of a form driven operating system of said data transaction terminal, each form including at least one prompt customized to a desired transaction type;

said form driven operating system controlling said data transaction terminal to accept input data of said desired transaction type using control data comprising at least one of said forms from said form memory;

a user selecting one of said menus using a data input device and said user selecting from said one menu at least one of said at least one form, another menu, and an updating process for further processing;

if said updating process is selected from said one menu by said user, downloading data streams to update said menus and forms in accordance with said desired transaction type; and if said at least one form is selected from said one menu by said user, said form driven operating system presenting to a display a form for eliciting data input of said desired transaction type from said user, said user inputting data in response to said at least one prompt of said form using said data input device, and said form driven operating system formatting at least said input data from said user into a data transaction for transmission to said remote database and transmitting said data transaction to said remote database.

40. A method as in claim 39, comprising the additional steps of:

receiving said data transaction at said remote database;

creating from said data transaction, depending on said desired transaction type, at least one additional data transaction containing data for a particular record in said remote database; and storing said at least one additional data transaction in said particular record.

41. A method as in claim 40, comprising the additional steps of:

creating from said data transaction, depending on said desired transaction type, at least one ancillary data transaction containing data for a particular record in an ancillary database different from said remote database; and storing said at least one ancillary data transaction in said particular record in said ancillary database.

42. A method as in claim 39, comprising the additional steps of:

sending a data request to a database server of said remote database; and said database server accessing data corresponding to said data request in said remote database and returning one of data responsive to said data request, a list of options for selection by said user, a value calculated from data contained in said data request, and a data report.

43. A terminal as in claim 28, wherein said remote database server is a remote phone mail system and said telephone circuit makes a telephone connection to said remote phone mail system, said data request being sent via said telephone connection and including a request for a visual representation of selection options of a phone mail menu of said remote phone mail system, and, in response to said data request, said remote phone mail system returning via said telephone connection a data stream containing said visual representation of said selection options of said phone mail menu, said visual representation of said selection options of said phone mail menu being presented to said display by said data transaction assembler for selection by said user using said data input device, and said data transaction assembler further sending data to said remote phone mail system via said telephone connection indicating which selection option was selected from said phone mail menu by said user.

44. A terminal as in claim 43, wherein said remote phone mail system returns a data stream containing a visual representation of selection options of a next phone mail menu via said telephone connection in response to said data indicating which selection option was selected from said phone mail menu by said user.

* * * * *

UNITED STATES PATENT AND TRADEMARK OFFICE
CERTIFICATE OF CORRECTION

PATENT NO.   : 5,805,676
DATED        : September 8, 1998
INVENTOR(S)  : Rocco L. Matino It is certified that error appears in the above-identified patent and that said Letters Patent is hereby corrected as shown below:

Column 10,
Line 42, change "110-13" to -- 110-113 --.

Column 12,
Line 12, change "600" to -- 60° --

Column 16,
Line 53, "The data stream entered etc." does not start a new paragraph.

Signed and Sealed this

Twenty-seventh Day of May, 2003

JAMES E. ROGAN
*Director of the United States Patent and Trademark Office*